US010512392B2

(12) United States Patent
Gurusamy et al.

(10) Patent No.: US 10,512,392 B2
(45) Date of Patent: Dec. 24, 2019

(54) SEGMENTED INSTRUMENT HAVING BRAKING CAPABILITIES

(75) Inventors: Jay Gurusamy, Santa Clara, CA (US); Carson Jay Shellberger, Raleigh, NC (US); Christopher A. Julian, Los Gatos, CA (US); Joshua Oeh, Fremont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 867 days.

(21) Appl. No.: 12/866,309

(22) PCT Filed: Feb. 6, 2009

(86) PCT No.: PCT/US2009/033446
§ 371 (c)(1),
(2), (4) Date: Oct. 21, 2010

(87) PCT Pub. No.: WO2009/100368
PCT Pub. Date: Aug. 13, 2009

(65) Prior Publication Data
US 2011/0295065 A1    Dec. 1, 2011

Related U.S. Application Data

(60) Provisional application No. 61/026,628, filed on Feb. 6, 2008.

(51) Int. Cl.
*A61B 1/00*    (2006.01)
*A61B 1/005*    (2006.01)
(Continued)

(52) U.S. Cl.
CPC ............ *A61B 1/0053* (2013.01); *A61B 1/008* (2013.01); *A61B 1/0055* (2013.01);
(Continued)

(58) Field of Classification Search
CPC ... A61B 1/0053; A61B 1/0055; A61B 1/0056; A61B 1/0057; A61B 1/0058; A61B 2017/00314
(Continued)

(56) References Cited

U.S. PATENT DOCUMENTS 616,672 A    12/1898  Kelling
2,241,576 A    5/1941  Charles
(Continued)

FOREIGN PATENT DOCUMENTS

DE    2823025 C2    2/1986
DE    3707787 A1    9/1988
(Continued)

OTHER PUBLICATIONS

"Active endoscope (ELASTOR, shape memory alloy robot)," 9 pages including 3 figures and 4 photographs. Accessed Feb. 21, 2002. Internet: http://mozu.mes.titech.ac.jp/research/medical/endoscope/endoscope.html.
(Continued)

*Primary Examiner* — Alexandra L Newton
(74) *Attorney, Agent, or Firm* — Jones Robb, PLLC

(57) ABSTRACT

One embodiment of present invention is a segmented instrument having braking capabilities that includes an elongate body having a plurality of links and a hinge connecting a pair of adjacent links in the plurality of links. There is also brake assembly coupled to each link in the pair of adjacent links and positioned to span the distance between the pair of adjacent links. Another embodiment of the present invention is a segmented instrument having a plurality of links and at least one lockable and articulatable joint positioned to connect a pair of adjacent links in the plurality of links. In addition, the at least one lockable and articulatable joint is adapted and configured to increase the number of frictional
(Continued)

surfaces available between the pair of adjacent links. There are also provided methods for controlling a segmented instrument. Exemplary steps of the method include introducing a segmented instrument into a patient where the segmented instrument has a plurality of links wherein adjacent links are joined by a hinge. Next, there is the step of manipulating the links about the hinges to maneuver the segmented instrument to provide access to a surgical site within the patient. In one aspect, the manipulating step produces a sliding motion between a plurality of complementary shaped components within a portion of a brake assembly between adjacent links. Next there is the step of actuating the brake assembly to substantially prevent movement about the hinge of the links attached to the braking mechanism.

23 Claims, 20 Drawing Sheets

(51) Int. Cl.
*A61B 1/008* (2006.01)
*A61B 1/273* (2006.01)
*A61B 1/04* (2006.01)
*G02B 23/24* (2006.01)

(52) U.S. Cl.
CPC ............ *A61B 1/0057* (2013.01); *A61B 1/042* (2013.01); *A61B 1/2736* (2013.01); *G02B 23/2476* (2013.01)

(58) Field of Classification Search
USPC ................ 600/114, 121–125, 141–142, 148, 600/227–229; 604/258, 95.04, 528; 606/1; 901/23
See application file for complete search history.

(56) References Cited

U.S. PATENT DOCUMENTS

| | | | |
|---|---|---|---|
| 2,510,198 A | 6/1950 | Tesmer | |
| 2,533,494 A | 12/1950 | Mitchell, Jr. | |
| 2,767,705 A | 10/1956 | Moore | |
| 3,060,972 A | 10/1962 | Sheldon | |
| 3,071,161 A | 1/1963 | Ulrich | |
| 3,096,962 A | 7/1963 | Meijs | |
| 3,162,214 A | 12/1964 | Bazinet | |
| 3,168,274 A | 2/1965 | Street | |
| 3,190,286 A | 6/1965 | Stokes | |
| 3,266,059 A * | 8/1966 | Stelle | 623/62 |
| 3,430,662 A | 3/1969 | Guarnaschelli | |
| 3,497,083 A | 2/1970 | Anderson | |
| 3,546,961 A | 12/1970 | Marton | |
| 3,610,231 A | 10/1971 | Takahashi et al. | |
| 3,625,084 A | 12/1971 | Siebert | |
| 3,643,653 A | 2/1972 | Nagashige et al. | |
| 3,739,770 A | 6/1973 | Mori | |
| 3,773,034 A | 11/1973 | Burns et al. | |
| 3,858,578 A | 1/1975 | Milo | |
| 3,897,775 A | 8/1975 | Furihata | |
| 3,913,565 A | 10/1975 | Kawahara | |
| 3,946,727 A | 3/1976 | Okada et al. | |
| 4,054,128 A | 10/1977 | Seufert et al. | |
| 4,176,662 A | 12/1979 | Frazer | |
| 4,236,509 A | 12/1980 | Takahashi et al. | |
| 4,240,435 A | 12/1980 | Yazawa et al. | |
| 4,272,873 A | 6/1981 | Dietrich | |
| 4,273,111 A | 6/1981 | Tsukaya | |
| 4,286,585 A | 9/1981 | Ogawa | |
| 4,327,711 A | 5/1982 | Takagi | |
| 4,366,810 A | 1/1983 | Slanetz, Jr. | |
| 4,393,728 A | 7/1983 | Larson et al. | |
| 4,432,349 A | 2/1984 | Oshiro | |
| 4,489,826 A | 12/1984 | Dubson | |
| 4,494,417 A | 1/1985 | Larson et al. | |
| 4,499,895 A | 2/1985 | Takayama | |
| 4,503,842 A | 3/1985 | Takayama | |
| 4,543,090 A | 9/1985 | McCoy | |
| 4,551,061 A | 11/1985 | Olenick | |
| 4,559,928 A | 12/1985 | Takayama | |
| 4,566,843 A | 1/1986 | Iwatsuka et al. | |
| 4,577,621 A | 3/1986 | Patel | |
| 4,592,341 A | 6/1986 | Omagari et al. | |
| 4,601,283 A | 7/1986 | Chikama | |
| 4,601,705 A | 7/1986 | McCoy | |
| 4,621,618 A | 11/1986 | Omagari | |
| 4,624,243 A | 11/1986 | Lowery et al. | |
| 4,630,649 A | 12/1986 | Oku | |
| 4,643,184 A | 2/1987 | Mobin-Uddin | |
| 4,646,722 A | 3/1987 | Silverstein et al. | |
| 4,648,733 A | 3/1987 | Merkt | |
| 4,651,718 A | 3/1987 | Collins et al. | |
| 4,655,257 A | 4/1987 | Iwashita | |
| 4,683,773 A | 8/1987 | Diamond | |
| 4,686,963 A | 8/1987 | Cohen et al. | |
| 4,712,969 A | 12/1987 | Kimura | |
| 4,753,222 A | 6/1988 | Morishita | |
| 4,753,223 A | 6/1988 | Bremer | |
| 4,787,369 A | 11/1988 | Allred, III | |
| 4,788,967 A | 12/1988 | Ueda | |
| 4,790,624 A | 12/1988 | Van Hoye et al. | |
| 4,793,326 A | 12/1988 | Shishido | |
| 4,796,607 A | 1/1989 | Allred, III | |
| 4,799,474 A | 1/1989 | Ueda | |
| 4,815,450 A | 3/1989 | Patel | |
| 4,832,473 A | 5/1989 | Ueda | |
| 4,834,068 A | 5/1989 | Gottesman | |
| 4,846,573 A | 7/1989 | Taylor et al. | |
| 4,873,965 A | 10/1989 | Danieli | |
| 4,873,990 A | 10/1989 | Holmes et al. | |
| 4,879,991 A | 11/1989 | Ogiu | |
| 4,884,557 A | 12/1989 | Takehana et al. | |
| 4,890,602 A | 1/1990 | Hake | |
| 4,895,431 A | 1/1990 | Tsujiuchi et al. | |
| 4,899,731 A | 2/1990 | Takayama et al. | |
| 4,904,048 A | 2/1990 | Sogawa et al. | |
| 4,930,494 A | 6/1990 | Takehana et al. | |
| 4,949,927 A | 8/1990 | Madocks et al. | |
| 4,957,486 A | 9/1990 | Davis | |
| 4,969,709 A | 11/1990 | Sogawa et al. | |
| 4,971,035 A | 11/1990 | Ito | |
| 4,977,886 A | 12/1990 | Takehana et al. | |
| 4,977,887 A | 12/1990 | Gouda | |
| 4,987,314 A | 1/1991 | Gotanda et al. | |
| 5,005,558 A | 4/1991 | Aomori | |
| 5,018,509 A | 5/1991 | Suzuki et al. | |
| 5,060,632 A | 10/1991 | Hibino et al. | |
| 5,090,956 A | 2/1992 | McCoy | |
| 5,092,901 A | 3/1992 | Hunter et al. | |
| 5,125,395 A | 6/1992 | Adair | |
| 5,127,393 A | 7/1992 | McFarlin et al. | |
| 5,159,446 A | 10/1992 | Hibino et al. | |
| 5,174,276 A | 12/1992 | Crockard | |
| 5,174,277 A | 12/1992 | Matsumaru | |
| 5,188,111 A | 2/1993 | Yates et al. | |
| 5,207,695 A | 5/1993 | Trout, III | |
| 5,217,001 A | 6/1993 | Nakao et al. | |
| 5,220,911 A | 6/1993 | Tamura | |
| 5,228,429 A | 7/1993 | Hatano | |
| 5,239,982 A | 8/1993 | Trauthen | |
| 5,243,967 A | 9/1993 | Hibino | |
| 5,250,167 A | 10/1993 | Adolf et al. | |
| 5,251,611 A | 10/1993 | Zehel et al. | |
| 5,253,647 A | 10/1993 | Takahashi et al. | |
| 5,257,617 A | 11/1993 | Takahashi | |
| 5,268,082 A | 12/1993 | Oguro et al. | |
| 5,271,381 A | 12/1993 | Ailinger et al. | |
| 5,271,382 A | 12/1993 | Chikama | |
| 5,297,443 A | 3/1994 | Wentz | |
| 5,325,845 A | 7/1994 | Adair | |
| 5,337,732 A | 8/1994 | Grundfest et al. | |

(56) References Cited

U.S. PATENT DOCUMENTS

| | | |
|---|---|---|
| 5,337,733 A | 8/1994 | Bauerfeind et al. |
| 5,343,874 A | 9/1994 | Picha et al. |
| 5,347,987 A | 9/1994 | Feldstein et al. |
| 5,348,259 A | 9/1994 | Blanco et al. |
| 5,368,015 A | 11/1994 | Wilk |
| 5,370,108 A | 12/1994 | Miura et al. |
| 5,383,467 A | 1/1995 | Auer et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,396,879 A | 3/1995 | Wilk et al. |
| 5,400,769 A | 3/1995 | Tanii et al. |
| 5,402,768 A | 4/1995 | Adair |
| 5,413,108 A | 5/1995 | Alfano |
| 5,421,337 A | 6/1995 | Richards-Kortum et al. |
| 5,429,118 A | 7/1995 | Cole et al. |
| 5,431,645 A | 7/1995 | Smith et al. |
| 5,439,000 A | 8/1995 | Gunderson et al. |
| 5,460,166 A | 10/1995 | Yabe et al. |
| 5,460,168 A | 10/1995 | Masubuchi et al. |
| 5,469,840 A | 11/1995 | Tanii et al. |
| 5,479,930 A | 1/1996 | Gruner et al. |
| 5,482,029 A * | 1/1996 | Sekiguchi et al. ............ 600/109 |
| 5,486,182 A | 1/1996 | Nakao et al. |
| 5,487,757 A | 1/1996 | Truckai et al. |
| 5,492,131 A | 2/1996 | Galel |
| 5,507,287 A | 4/1996 | Palcic et al. |
| 5,507,717 A | 4/1996 | Kura et al. |
| 5,522,788 A | 6/1996 | Kuzmak |
| 5,531,664 A | 7/1996 | Adachi et al. |
| 5,535,759 A | 7/1996 | Wilk |
| 5,551,945 A | 9/1996 | Yabe et al. |
| 5,556,370 A | 9/1996 | Maynard |
| 5,556,700 A | 9/1996 | Kaneto et al. |
| 5,558,619 A | 9/1996 | Kami et al. |
| 5,558,665 A | 9/1996 | Kieturakis |
| 5,577,992 A | 11/1996 | Chiba et al. |
| 5,590,660 A | 1/1997 | MacAulay et al. |
| 5,601,087 A | 2/1997 | Gunderson et al. |
| 5,602,449 A | 2/1997 | Krause et al. |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,631,040 A | 5/1997 | Takuchi et al. |
| 5,645,520 A | 7/1997 | Nakamura et al. |
| 5,647,368 A | 7/1997 | Zeng et al. |
| 5,651,366 A | 7/1997 | Liang et al. |
| 5,658,238 A | 8/1997 | Suzuki et al. |
| 5,662,587 A | 9/1997 | Grundfest et al. |
| 5,662,621 A | 9/1997 | Lafontaine |
| 5,665,050 A | 9/1997 | Benecke |
| 5,667,476 A | 9/1997 | Frassica et al. |
| 5,679,216 A | 10/1997 | Takayama et al. |
| 5,728,044 A | 3/1998 | Shan |
| 5,733,245 A | 3/1998 | Kawano |
| 5,749,828 A * | 5/1998 | Solomon ............ A61B 1/0055 600/139 |
| 5,752,912 A | 5/1998 | Takahashi et al. |
| 5,759,151 A | 6/1998 | Sturges |
| 5,762,613 A | 6/1998 | Sutton et al. |
| 5,769,792 A | 6/1998 | Palcic et al. |
| 5,771,902 A | 6/1998 | Lee et al. |
| 5,772,597 A | 6/1998 | Goldberger et al. |
| 5,779,624 A | 7/1998 | Chang |
| 5,807,241 A | 9/1998 | Heimberger |
| 5,810,715 A | 9/1998 | Moriyama |
| 5,810,716 A | 9/1998 | Mukherjee et al. |
| 5,810,717 A | 9/1998 | Maeda et al. |
| 5,813,976 A | 9/1998 | Filipi et al. |
| 5,819,749 A | 10/1998 | Lee et al. |
| 5,827,190 A | 10/1998 | Palcic et al. |
| 5,827,265 A | 10/1998 | Glinsky et al. |
| 5,842,973 A | 12/1998 | Bullard |
| 5,855,565 A | 1/1999 | Bar-Cohen et al. |
| 5,857,962 A | 1/1999 | Bracci et al. |
| 5,860,914 A | 1/1999 | Chiba et al. |
| 5,868,760 A | 2/1999 | McGuckin, Jr. |
| 5,873,817 A | 2/1999 | Kokish et al. |
| 5,876,329 A | 3/1999 | Harhen |
| 5,876,373 A | 3/1999 | Giba et al. |
| 5,885,208 A | 3/1999 | Moriyama |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,911,715 A | 6/1999 | Berg et al. |
| 5,916,146 A | 6/1999 | Allotta et al. |
| 5,916,147 A * | 6/1999 | Boury ............... A61M 25/0147 600/139 |
| 5,921,915 A | 7/1999 | Aznoian et al. |
| 5,928,136 A | 7/1999 | Barry |
| 5,941,815 A | 8/1999 | Chang |
| 5,941,908 A | 8/1999 | Goldsteen et al. |
| 5,957,833 A | 9/1999 | Shan |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,996,346 A | 12/1999 | Maynard |
| 6,033,359 A | 3/2000 | Doi |
| 6,036,636 A | 3/2000 | Motoki et al. |
| 6,036,702 A | 3/2000 | Bachinski et al. |
| 6,042,155 A | 3/2000 | Lockwood |
| 6,048,307 A | 4/2000 | Grundl et al. |
| 6,066,102 A | 5/2000 | Townsend et al. |
| 6,066,132 A | 5/2000 | Chen et al. |
| 6,071,234 A | 6/2000 | Takada |
| 6,096,023 A | 8/2000 | Lemelson |
| 6,096,289 A | 8/2000 | Goldenberg |
| 6,099,464 A | 8/2000 | Shimizu et al. |
| 6,099,485 A | 8/2000 | Patterson |
| 6,106,510 A | 8/2000 | Lunn et al. |
| 6,109,852 A | 8/2000 | Shahinpoor et al. |
| 6,117,296 A | 9/2000 | Thomson |
| 6,129,667 A | 10/2000 | Dumoulin et al. |
| 6,129,683 A | 10/2000 | Sutton et al. |
| 6,141,577 A | 10/2000 | Rolland et al. |
| 6,149,581 A | 11/2000 | Klingenstein |
| 6,162,171 A | 12/2000 | Ng et al. |
| 6,174,280 B1 | 1/2001 | Oneda et al. |
| 6,174,291 B1 | 1/2001 | McMahon et al. |
| 6,179,776 B1 | 1/2001 | Adams et al. |
| 6,201,989 B1 | 3/2001 | Whitehead et al. |
| 6,203,493 B1 | 3/2001 | Ben-Haim |
| 6,210,337 B1 | 4/2001 | Dunham et al. |
| 6,221,006 B1 | 4/2001 | Dubrul et al. |
| 6,249,076 B1 | 6/2001 | Madden et al. |
| 6,264,086 B1 | 7/2001 | McGuckin, Jr. |
| 6,270,453 B1 | 8/2001 | Sakai |
| 6,293,907 B1 | 9/2001 | Axon et al. |
| 6,306,081 B1 | 10/2001 | Ishikawa et al. |
| 6,309,346 B1 | 10/2001 | Farhadi |
| 6,315,714 B1 | 11/2001 | Akiba |
| 6,327,492 B1 | 12/2001 | Lemelson |
| 6,332,089 B1 | 12/2001 | Acker et al. |
| 6,348,058 B1 | 2/2002 | Melkent et al. |
| 6,366,799 B1 | 4/2002 | Acker et al. |
| 6,402,687 B1 | 6/2002 | Ouchi |
| 6,408,889 B1 | 6/2002 | Komachi |
| 6,428,203 B1 | 8/2002 | Danley |
| 6,428,470 B1 | 8/2002 | Thompson |
| 6,453,190 B1 | 9/2002 | Acker et al. |
| 6,459,481 B1 | 10/2002 | Schaack |
| 6,468,203 B2 | 10/2002 | Belson |
| 6,482,149 B1 | 11/2002 | Torii |
| 6,485,413 B1 | 11/2002 | Boppart et al. |
| 6,485,496 B1 | 11/2002 | Suyker et al. |
| 6,490,467 B1 | 12/2002 | Bucholz et al. |
| 6,503,259 B2 | 1/2003 | Huxel et al. |
| 6,511,418 B2 | 1/2003 | Shahidi et al. |
| 6,514,237 B1 | 2/2003 | Maseda |
| 6,527,706 B2 | 3/2003 | Ide |

(56) References Cited

U.S. PATENT DOCUMENTS

| | | |
|---|---|---|
| 6,547,723 B1 | 4/2003 | Ouchi |
| 6,554,793 B1 | 4/2003 | Pauker et al. |
| 6,610,007 B2 | 8/2003 | Belson et al. |
| 6,616,600 B2 | 9/2003 | Pauker |
| 6,638,213 B2 | 10/2003 | Ogura et al. |
| 6,641,528 B2 | 11/2003 | Torii |
| 6,679,836 B2 | 1/2004 | Couvillon, Jr. |
| 6,699,183 B1 | 3/2004 | Wimmer |
| 6,761,685 B2 | 7/2004 | Adams et al. |
| 6,783,491 B2 * | 8/2004 | Saadat .............. A61B 1/0008 600/114 |
| 6,790,173 B2 | 9/2004 | Saadat et al. |
| 6,793,621 B2 | 9/2004 | Butler et al. |
| 6,800,056 B2 | 10/2004 | Tartaglia et al. |
| 6,835,173 B2 | 12/2004 | Couvillon, Jr. |
| 6,837,846 B2 | 1/2005 | Jaffe et al. |
| 6,837,847 B2 | 1/2005 | Ewers et al. |
| 6,843,793 B2 | 1/2005 | Brock et al. |
| 6,850,794 B2 | 2/2005 | Shahidi |
| 6,858,005 B2 | 2/2005 | Ohline et al. |
| 6,875,170 B2 | 4/2005 | Francois et al. |
| 6,890,297 B2 | 5/2005 | Belson |
| 7,090,637 B2 * | 8/2006 | Danitz et al. .............. 600/141 |
| 8,298,161 B2 * | 10/2012 | Vargas .......................... 600/587 |
| 8,388,520 B2 * | 3/2013 | Stefanchik et al. ........ 600/144 |
| 2001/0000040 A1 | 3/2001 | Adams et al. |
| 2002/0022765 A1 | 2/2002 | Belson |
| 2002/0062062 A1 | 5/2002 | Belson et al. |
| 2002/0062063 A1 | 5/2002 | Ogura et al. |
| 2002/0120178 A1 | 8/2002 | Tartaglia et al. |
| 2002/0120254 A1 | 8/2002 | Julian et al. |
| 2002/0147385 A1 | 10/2002 | Butler et al. |
| 2002/0151767 A1 | 10/2002 | Sonnenschein et al. |
| 2002/0161281 A1 | 10/2002 | Jaffe et al. |
| 2002/0169361 A1 | 11/2002 | Taniguchi et al. |
| 2002/0193661 A1 | 12/2002 | Belson |
| 2002/0193662 A1 | 12/2002 | Belson |
| 2003/0032859 A1 | 2/2003 | Belson |
| 2003/0045778 A1 | 3/2003 | Ohline et al. |
| 2003/0083550 A1 | 5/2003 | Miyagi |
| 2003/0130598 A1 | 7/2003 | Manning et al. |
| 2003/0149338 A1 | 8/2003 | Francois et al. |
| 2003/0195387 A1 | 10/2003 | Kortenbach et al. |
| 2003/0233027 A1 | 12/2003 | Ewers et al. |
| 2003/0233056 A1 | 12/2003 | Saadat et al. |
| 2003/0233057 A1 | 12/2003 | Saadat et al. |
| 2003/0233058 A1 | 12/2003 | Ewers et al. |
| 2003/0233066 A1 * | 12/2003 | Ewers et al. .................. 604/27 |
| 2003/0236505 A1 | 12/2003 | Bonadio et al. |
| 2003/0236549 A1 | 12/2003 | Bonadio et al. |
| 2004/0044270 A1 | 3/2004 | Barry |
| 2004/0054322 A1 * | 3/2004 | Vargas .......................... 600/585 |
| 2004/0106852 A1 | 6/2004 | Windheuser et al. |
| 2004/0176683 A1 | 9/2004 | Whitin et al. |
| 2004/0193008 A1 | 9/2004 | Jaffe et al. |
| 2004/0193009 A1 | 9/2004 | Jaffe et al. |
| 2005/0041048 A1 * | 2/2005 | Hillman ............... F16M 11/08 345/108 |
| 2005/0065397 A1 * | 3/2005 | Saadat et al. .............. 600/104 |
| 2005/0085693 A1 | 4/2005 | Belson et al. |
| 2006/0052664 A1 | 3/2006 | Julian et al. |
| 2007/0015965 A1 | 1/2007 | Cox et al. |
| 2007/0135803 A1 * | 6/2007 | Belson ............................. 606/1 |
| 2007/0270650 A1 | 11/2007 | Eno et al. |
| 2009/0099420 A1 | 4/2009 | Woodley et al. |
| 2009/0124857 A1 * | 5/2009 | Viola ............................ 600/141 |

FOREIGN PATENT DOCUMENTS

| | | |
|---|---|---|
| DE | 4102211 A1 | 8/1991 |
| DE | 19729499 A1 | 1/1999 |
| EP | 497781 A1 | 8/1992 |
| ES | 2048086 A | 3/1994 |
| ES | 2062930 A | 12/1994 |
| FR | 2732225 A1 | 10/1996 |
| FR | 2807960 A1 | 10/2001 |
| JP | 63136014 A2 | 6/1988 |
| JP | 63272322 A2 | 11/1988 |
| JP | 2296209 A2 | 12/1990 |
| JP | 3004830 A2 | 1/1991 |
| JP | 3109021 A2 | 5/1991 |
| JP | 3139325 A2 | 6/1991 |
| JP | 3170125 A2 | 7/1991 |
| JP | 5001999 A2 | 1/1993 |
| JP | 5011196 A2 | 1/1993 |
| JP | 5111458 A2 | 5/1993 |
| JP | 5177002 A2 | 7/1993 |
| JP | 5184531 A2 | 7/1993 |
| JP | 5305073 A2 | 11/1993 |
| JP | 7088788 A2 | 4/1995 |
| JP | 7120684 A2 | 5/1995 |
| JP | 8010336 A2 | 1/1996 |
| JP | 8066351 A2 | 3/1996 |
| JP | 8322783 A2 | 12/1996 |
| JP | 8322786 A2 | 12/1996 |
| JP | 10014863 A2 | 1/1998 |
| JP | 11042258 A2 | 2/1999 |
| JP | 11048171 A | 2/1999 |
| JP | 21096478 A2 | 4/2001 |
| SU | 871786 A1 | 10/1981 |
| SU | 1256955 A1 | 9/1986 |
| SU | 1301701 A1 | 4/1987 |
| WO | 9315648 A1 | 8/1993 |
| WO | 199317751 A1 | 9/1993 |
| WO | 199419051 A1 | 9/1994 |
| WO | 199504556 A2 | 2/1995 |
| WO | 199710746 A1 | 3/1997 |
| WO | 199811816 A1 | 3/1998 |
| WO | 199933392 A1 | 7/1999 |
| WO | 199951283 A2 | 10/1999 |
| WO | 199959664 A1 | 11/1999 |
| WO | 200054653 A1 | 9/2000 |
| WO | 200074565 A1 | 12/2000 |
| WO | 200149353 A2 | 7/2001 |
| WO | 200158973 A2 | 8/2001 |
| WO | 200167964 A2 | 9/2001 |
| WO | 200170096 A1 | 9/2001 |
| WO | 200170097 A1 | 9/2001 |
| WO | 200174235 A1 | 10/2001 |
| WO | 200180935 A1 | 11/2001 |
| WO | 200224058 A2 | 3/2002 |
| WO | 200239909 A1 | 5/2002 |
| WO | 200247549 A1 | 6/2002 |
| WO | 200264028 A1 | 8/2002 |
| WO | 200268988 A1 | 9/2002 |
| WO | 200269841 A2 | 9/2002 |
| WO | 200289692 A1 | 11/2002 |
| WO | 200296276 A1 | 12/2002 |
| WO | 200328547 A2 | 4/2003 |
| WO | 200373920 A2 | 9/2003 |
| WO | 200373921 A1 | 9/2003 |
| WO | 200392476 A2 | 11/2003 |
| WO | 200406980 A2 | 1/2004 |
| WO | 200449905 A2 | 6/2004 |
| WO | 200471284 A1 | 8/2004 |
| WO | 200480313 A1 | 9/2004 |
| WO | 200484702 A2 | 10/2004 |
| WO | 200633109 A2 | 3/2006 |
| WO | 200997461 | 8/2009 |
| WO | 2009100368 A1 | 8/2009 |

OTHER PUBLICATIONS

Bar-Cohen, J., "EAP applications, potential, and challenges," Chapter 21 in Electroactive Polymer (EAP) Actuators as Artificial Muscles, Bar-Cohen, Ed., SPIE Press, 2001, pp. 615-659.

Bar-Cohen, Y., "EAP history, current status, and infrastructure," Chapter 1 in Electroactive Polymer (EAP) Actuators as Artificial Muscles, Bar-Cohen Ed., SPIE Press, 2001, pp. 3-44.

Bar-Cohen, Y. Ed., Worldwide ElectroActive Polymers (Artificial Muscles) Newsletter, Jun. 2001, vol. 3, issue 1, pp. 1-14.

(56) References Cited

OTHER PUBLICATIONS

Bar-Cohen, Y., "Transition of EAP material from novelty to practical applications—are we there yet" Smart Structures and Materials 2001: Electroactive Polymer Actuators and Devices, Yoseph Bar-Cohen Ed., Proceedings of SPIE, Mar. 5-8, 2001, vol. 4329, pp. 1-6.
Brock, D.L., "Review of artificial muscle based on contractile polymers," MIT Artificial Intelligence Laboratory, A.I.Memo No. 1330, Nov. 1991, 10 pages. Accessed Jun. 23, 2005. Internet: http://www.ai.mit.edu/projects/muscle/papers/memo1330/memo1330.html.
Cho, S. et al., "Development of micro inchworm robot actuated by electrostrictive polymer actuator," Smart Structures and Materials 2001: Electroactive Polymer Actuators and Devices, Yoseph Bar-Cohen Ed., Proceedings of SPIE, Mar. 5-8, 2001, vol. 4329, pp. 466-474.
Duntgen, C., "Walking machines: 0-legged-robots: A compilation by Christian Duntgen," Aug. 26, 2000, 16 pages.
EP09707247 Extended European Search Report dated Jan. 9, 2013, 8 pages.
EP11175098 Extended EP Search Report dated Dec. 1, 2011, 7 pages.
Grecu, E. et al., "Snake-like flexible Micro-robot," Copernicus project presentation, financed by European Community, Project start May 1, 1995, 6 pages. Accessed Dec. 27, 2001; Internet: http://www.agip.sciences.univ-metz.fr/~mihalach/Copernicus_project_engl.html.
Hasson, H.M., "Technique of Open Laparoscopy," (from step 1 to step 9), May 1979, 2424 North Clark Street, Chicago, Illinois 60614, 3 pages.
Ikuta, Koji et al., "Shape memory alloy servo actuator system with electric resistance feedback and application for active endoscope," Proc. IEEE International Conference on Robotics and Automation, 1988, pp. 427-430, vol. 1, IEEE.
Jager, E.W.H. et al., "Microfabricating conjugated polymer actuators," Science, Nov. 24, 2000, vol. 290, pp. 1540-1545.
Jeon, J.W. et al., "Electrostrictive polymer actuators and their control systems," Smart Structures and Materials 2001: Electroactive Polymer Actuators and Devices, Yoseph-Bar Cohen Ed., Proceedings of SPIE, Mar. 5-8, 2001, vol. 4329, pp. 380-388.
Klaassen, B., "GMD-Snake: Robot snake with a flexible real-time control," AiS—GMD-Snake, last updated Oct. 17, 2001, 3 pages, accessed Dec. 27, 2001; Internet: http://ais.gmd.de/BAR/snake.html.
Kornbluh, R. et al., "Application of dielectric elastomer EAP actuators,"Chapter 16 in Electroactive Polymer (EAP) Actuators as Artificial Muscles, Yoseph Bar-Cohen, Ed., SPIE Press, 2001, pp. 457-495.
Kubler, C. et al., "Endoscopic robots," Proceedings of 3rd International Conference on Medical Image Computing and Computer-Assisted Intervention (MICCAI 2000), Oct. 11-14, 2000, in Lecture Notes in Computer Science, Springer, vol. 1935, pp. 949-955.
Laptop Magazine, Science & Technology section, Oct. 2002, pp. 98, 100, and 102.
Lee, Thomas S. et al., "A highly redundant robot system for inspection," Proceedings of Conference on Intelligent Robotics in Field, Factory, Service, and Space (CIRFFSS '94). Mar. 21-24, 1994. vol. 1, pp. 142-148. Houston, Texas.
Lightdale, C.J., "New developments in endoscopy," American College of Gastroenterology 65th Annual Scientific Meeting, Day 1, Oct. 16, 2000, pp. 1-9.
Madden, J.D.W., Abstract of "Conducting polymer actuators," Smart Structures and Materials 2001: Electroactive Polymer Actuators and Devices, Yoseph Bar-Cohen Ed., Proceedings of SPIE, Mar. 5-8, 2001, vol. 4329, 1 page.
Madden, J.D.W. et al., "Polypyrrole actuators: modeling and performance", Smart Structures and Materials 2001: Electroactive Polymer Actuators and Devices, Yoseph Bar-Cohen Ed., Proceedings of SPIE, Mar. 5-8, 2001, vol. 4329, pp. 72-83.
McKernan, J.B. et al., "Laparoscopic general surgery," Journal of the Medical Association of Georgia, Mar. 1990, vol. 79, Issue 3, pp. 157-159.
Nam, J.D., "Electroactive polymer (EAP) actuators and devices for micro-robot systems," Nov. 28, 2000, 1 page.
PCT/US02/29472 International Search Report, dated Mar. 6, 2003, 3 pages.
PCT/US03/06078 International Search Report, dated Aug. 13, 2003, 1 page.
PCT/US03/13600 International Search Report, dated Dec. 12, 2003, 1 page.
PCT/US03/27042 International Search Report, dated Feb. 4, 2004, 2 pages.
PCT/US03/37778 International Search Report, dated Feb. 8, 2005, 1 page.
PCT/US09/33446 International Search Report and Written Opinion of the International Searching Authority, dated Mar. 19, 2009, 9 pages.
Peirs, J. et al., "Miniature parallel manipulators for integration in a self-propelling endoscope," IUAP P4/24 IMechS Workshop, Organized by UCL/PRM, Oct. 27, 1999, 2 pages.
Pelrine, R. et al., "Applications of dielectric elastomer actuators," Smart Structures and Materials 2001: Electroactive Polymer Actuators and Devices, Yoseph Bar-Cohen Ed., Proceedings of SPIE, Mar. 5-8, 2001, vol. 4329, Issue 1, pp. 335-349.
Sansinena, J.M. et al., "Conductive polymers," Chapter 7 of Electroactive Polymer (EAP) Actuators as Artificial Muscles, Bar-Cohen Ed., SPIE Press, 2001, pp. 193-221.
Slatkin, A.B. et al., "The development of a robotic endoscope," Proceedings 1995 IEEE/RSJ International Conference on Intelligent Robots and Systems, Aug. 5-9, 1995, vol. 2, pp. 162-171, Pittsburgh, Pennsylvania.
Supplementary European Search Report of EP Patent Application No. EP03728638, dated Oct. 27, 2005, 2 pages total.
French language U.S. Appl. No. 09/556,673, Christian Francois et al., filed Apr. 21, 2000.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Zuccaro, G., "Procedural sedation in the GI suite," a conference co-sponsored by the American Society of Anesthesiologists, 16th Annual Meeting 2001, May 3-6, 2001, pp. 162-171.

\* cited by examiner

SEGMENTED INSTRUMENT HAVING BRAKING CAPABILITIES

CROSS REFERENCE TO RELATED APPLICATION

This application claims priority under 35 U.S.C. §§ 119(a) and 365(b) to International Application No. PCT/US2009/033446 (filed Feb. 6, 2009; entitled "A Segmented Instrument Having Braking Capabilities"), which claimed the benefit under §§ 119(e) and 120 of U.S. Patent Application No. 61/026,628 (filed Feb. 6, 2008; entitled "Vacuum Lock Technology").

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

Embodiments of the present invention provide articulating and lockable segmented instruments useful in perform surgical procedures in the body. The instruments described herein may articulate and then be locked into a desired configuration. In addition, there are also embodiments of the brake assemblies that provide articulation capabilities when not engaged and locking capabilities when engaged.

BACKGROUND OF THE INVENTION

Guide tubes may be used to support instruments disposed within them. Many conventional guide tubes provide some form of locking capability. However, conventional guide tubes provide a single surface lock engagement when locking. Such locking configurations may provide locking forces up to a point but are generally limited in the amount of locking force that may be generated. Some emerging forms of surgery may benefit from guide tubes or controllable instruments with locking or braking capabilities that provide not only improved articulation and control but also increased locking force.

SUMMARY OF THE INVENTION

Embodiments of the present invention may be useful while performing procedures within a patient, such as in natural orifice transluminal endoscopic surgical procedures, to provide a stable controllable and/or semi-rigid platform from which to perform the procedure. In contrast to conventional locking approaches, embodiments of the inventions described herein provide additional frictional surfaces or in some embodiments multiplied frictional surfaces between articulating components. The additional frictional force in turn increases the braking or locking force applied to the instrument. Various embodiments of the present invention provide mechanisms by which the user can selectively rigidize all or a portion of the elongate body through the use of multiple surfaces placed between articulating segments or individual links or vertebra. In addition, while the braking assemblies described herein provide multiplied friction and lock force, they remain capable of articulation when not engaged. In some embodiments, the brake assembly includes the hinge or portion of a hinge or joint used for the articulation of the segmented instrument.

In one aspect, there is provided a segmented instrument having a plurality of links and at least one lockable and articulatable joint positioned to connect a pair of adjacent links in the plurality of links. In addition, the at least one lockable and articulatable joint being adapted and configured to increase the number of frictional surfaces available between the pair of adjacent links. As described above, cables and coil pipes take up a large amount of space along the elongate body. In one aspect, the brake assembly lies on or in the exterior surface of the segment, hinge or vertebra in order to keep the interior portions of the instrument free.

In one embodiment of the present invention, there is a segmented instrument having braking capabilities. The instrument includes an elongate body having a plurality of links. The instrument may be configured as any of a wide variety of surgical devices. For example, the instrument may be an endoscope or other controllable instrument as described above or it may be a guide used to direct the movement or placement of another instrument including another segmented instrument. A hinge connects a pair of adjacent links in the plurality of links. There is a brake assembly coupled to each link in the pair of adjacent links. The brake assembly is positioned to span the distance between the pair of adjacent links.

A variety of different materials may be employed from which to make components in a brake assembly. The desired properties of the materials used in a brake assembly include lubricity between layers when the brake is not actuated (e.g., braking force is not applied or no vacuum is pulled) and sufficient friction to bind the components or brake assembly when the brake is actuated (e.g., the braking force is applied or a vacuum is pulled). Another useful property is that the brake assembly has the flexibility to bend when a joint is articulated. Exemplary materials for use in brake assembly components include, without limitation, aluminum, carbon fiber, and various plastics such as and without limitation Teflon®.

The brake assembly may be on all or only some of the links, vertebra or segments of an instrument. The brake assembly or multiple brake assemblies may be placed in isolated or only specific portions of the instrument. Numerous actuation mechanisms may be used to engage the brake assembly or assemblies. In one aspect, the brake assemblies are activated by pulling a cable running through or along the instrument. In another alternative form of activation, the interior of the scope (a normally sealed environment) is pumped down so that the interior is under vacuum. The action of the skin of the instrument being pulled in by the vacuum may be used to actuate a braking mechanism. In addition, the brake assemblies may be activated serially or simultaneously or in any order depending upon circumstances in use. The brake assembly or assemblies may be provided only in a distal portion of the links in the plurality of links. Alternatively, the brake assembly is provided only in a proximal portion of the links in the plurality of links. In still another alternative, the brake assembly is provided only in a middle portion of the links in the plurality of links.

The movement of the pair of adjacent links about the hinge is prevented when the brake assembly is engaged. In one aspect, the brake assembly is provided only between a portion of the links in the plurality of links. There are configurations of the braking assembly where one or more are placed wherein the actuation of the brake assembly removes one degree of freedom from a portion of the instrument. In other aspects, a plurality of brake assemblies are coupled to the instrument. In this example, the actuation of the plurality of brake assemblies substantially locks the shape of instrument by locking substantially all of the plurality of links in the instrument. In an alternative configuration, the plurality of brake assemblies are coupled to the instrument wherein actuation of the plurality of brake assemblies substantially removes one degree of freedom from the movement of the segmented instrument.

In addition, the brake assembly is adapted and configured to complement the operation of the hinge so that the hinge remains articulatable when the brake assembly is not actuated or engaged. The brake assembly is adapted and configured to increase the number of frictional surfaces between the pair of adjacent links. In some embodiments, there is a recessed portion on the surface of the each of links in the pair of adjacent links sized and shaped to conform to the size and shape of a portion of a component in the brake assembly. The size and shape of the recessed portion will vary with the particular brake assembly design implemented. By way of example, the recessed portion on the surface of the each of links in the pair of adjacent links has a generally rectangular shape or, alternatively, a generally arcurate shape.

The brake assembly is spaced apart from the at least one hinge. In one aspect, the brake assembly is spaced apart about 90 degrees about the circumference of the link from the at least one hinge. Practical limitations of the actual design of a specific instrument may alter the location of the braking mechanism. The spacing may be as close as practical to 90 degrees from the hinge location.

In some embodiments, the brake assembly may also include a plurality of complementary shaped components. The complementary shaped components may have surfaces adapted and configured to provide sliding motion when links move about the hinge. The complementary shaped components may come in virtually any shape and orientation that allow sliding, relative movement. In one example, the plurality of complementary shaped components may be provided by a plurality of interwoven slats. This is one example where the complementary surfaces are generally flat. In still another example, the complementary surfaces are generally arcurate. In still another aspect, a complementary shaped component positioned adjacent one link in the pair of links moves along with the movement of the other of the links in the pair of links.

In one aspect of the present invention, vacuum applied to the instrument is used to lock or rigidize the elongate body. In other aspects of the invention, a cable extending through or along the instrument is used to engage the brake assembly.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

In the drawings.

DETAILED DESCRIPTION OF THE INVENTION

Figure 1:
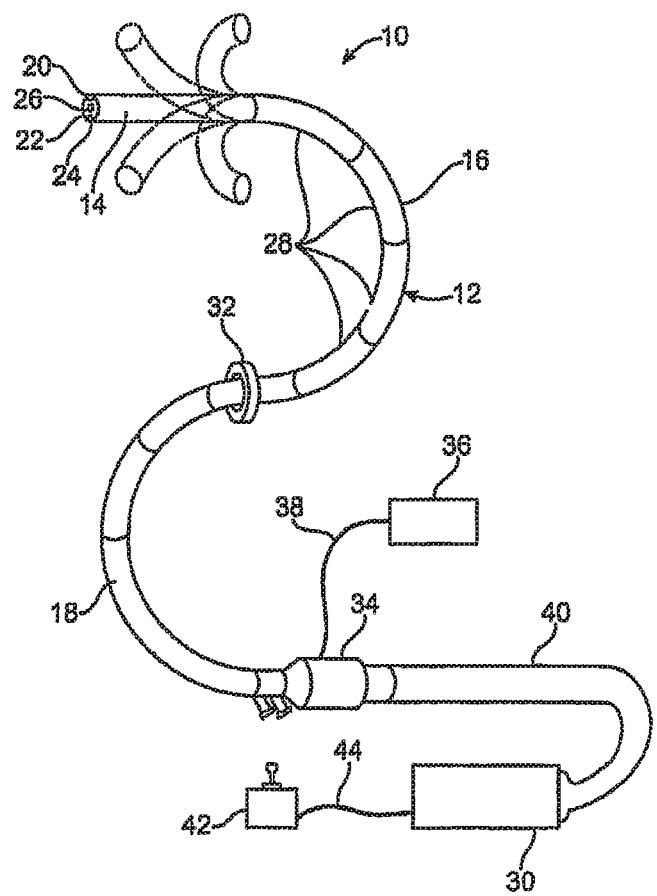
FIG. 1 illustrates an exemplary controllable segmented instrument and associated components of a control and interface system.

FIG. 1 depicts a flexible endoscope 10, in accordance with an embodiment of the present invention. Endoscope 10 has elongate body 12 with steerable distal portion 14, automatically controlled proximal portion 16, and flexible and passively manipulated proximal portion 18. The skilled artisan will appreciate that automatically controlled proximal portion 16 may also be flexible and passively manipulated, although it is preferred to provide automatically controlled proximal portion 16. The skilled artisan will also appreciate that elongate body 12 can have only steerable distal portion 14 and automatically controlled portion 16. Fiber optic imaging bundle 20 and illumination fiber(s) 22 may extend through elongate body 12 to steerable distal portion 14, or video camera 24 (e.g., CCD or CMOS camera) may be positioned at the distal end of steerable distal portion 14, as known by the skilled artisan. As the skilled artisan appreciates, a user views live or delayed video feed from video camera 24 via a video cable (e.g., wire or optical fiber, not shown) or through wireless transmission of the video signal. Typically, as will be appreciated by the skilled artisan, endoscope 10 will also include one or more access lumens, working channels, light channels, air and water channels, vacuum channels, and a host of other well known complements useful for both medical and industrial endoscopy. These channels and other amenities are shown generically as 26. In particular these amenities may include multiple tool channels in order to provide access for tools to a surgical site by passing the endoscope through a natural orifice proximate to a surgical target site, as in natural orifice transluminal (or transgastric) endoscopic surgery (NOTES).

Preferably, automatically controlled proximal portion 16 comprises a plurality of segments 28, which are controlled via computer and/or electronic controller 30. Such an automatically controlled endoscope is described in further detail in commonly assigned U.S. patent application Ser. No. 10/229,577 (now U.S. Pat. No. 6,858,005) and Ser. No. 11/750,988, both previously incorporated herein by reference. Preferably, the distal end of a tendon (more thoroughly described below) is mechanically connected to a each segment 28 or steerable distal portion 14, with the proximal end of the tendon mechanically connected to actuators to articulate segments 28 or steerable distal portion 14, which is more fully described below and in U.S. patent application Ser. No. 10/229,577 (now U.S. Pat. No. 6,858,005) and Ser. No. 11/750,988, both previously incorporated herein by reference. The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, electrical voltage, heat, etc., to each of the bundles to actuate a linear motion in the wire bundles which in turn actuate the tendon movement. The linear translation of the actuators within the controller may be configured to move over a relatively short distance to accomplish effective articulation depending upon the desired degree of segment movement and articulation. In addition, the skilled artisan will also appreciate that knobs attached to rack and pinion gearing can be used to actuate the tendons attached to steerable distal portion 14. An axial motion transducer 32 (also called a depth referencing device or datum) may be provided for measuring the axial motion, i.e., the depth change, of elongate body 12 as it is advanced and withdrawn. As elongate body 12 of endoscope 10 slides through axial motion transducer 32, it indicates the axial position of the elongate body 12 with respect to a fixed point of reference. Axial motion transducer 32 is more fully described in U.S. patent application Ser. Nos. 10/229,577 and 11/522,305, previously incorporated herein by reference. Additionally, an optical sensor may be used to determine the axial position of the endoscope, either alone or in combination with an optical shape sensor. In addition to the patents, patent applications, periodicals and other references cited below, NeoGuide Systems has designed a fully segmented controllable instrument. An exemplary instrument is described in U.S. Pat. No. 6,858,005 entitled Tendon Driven Endoscope. Additional details of a depth measurement system are described in U.S. patent application Ser. Nos. 10/988,212 and 10/384,252.

In the embodiment depicted in FIG. 1, handle 34 is connected to illumination source 36 by illumination cable 38 that is connected to or continuous with illumination fibers 22. Handle 34 is connected to electronic controller 30 by way of controller cable 40. Steering controller 42 (e.g., a joy stick) is connected to electronic controller 30 by way of second cable 44 or directly to handle 34. Electronic controller 30 controls the movement of the segmented automatically controlled proximal portion 16.

Figure 2:
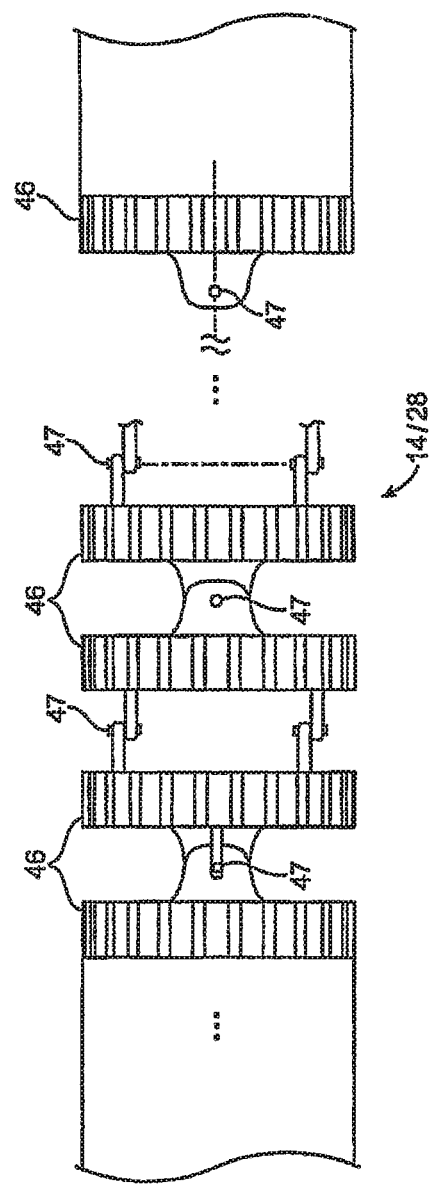
FIG. 2 is a view of a segment having a number of links joined by hinges.

Referring to FIG. 2, steerable distal portion 14 and segments 28 of automatically controlled proximal portion 16 are preferably constructed from a plurality of links 46. Five links 46 are shown in this example for the sake of clarity, although the skilled artisan will recognize that any number of links may be used including just one link, the ultimate number being primarily defined by the purpose for which segments 28 or steerable distal portion 14 will be used. Each joint 47 connects one link (e.g., 46) to an adjacent link (e.g., 46). Each link 46, in this embodiment, can move with one degree of freedom relative to an adjacent link, and more than one link hinged together provides two degrees of freedom.

Figure 3A:
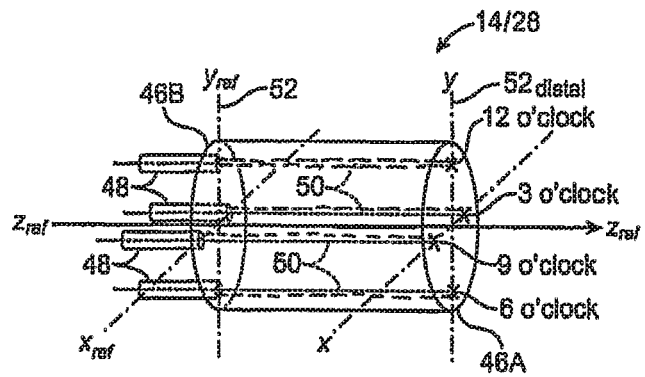
FIGS. 3A, 3B and 3C illustrate the movement of an exemplary segment thought the use of three actuation cables connected to the segment.
Figure 3B:
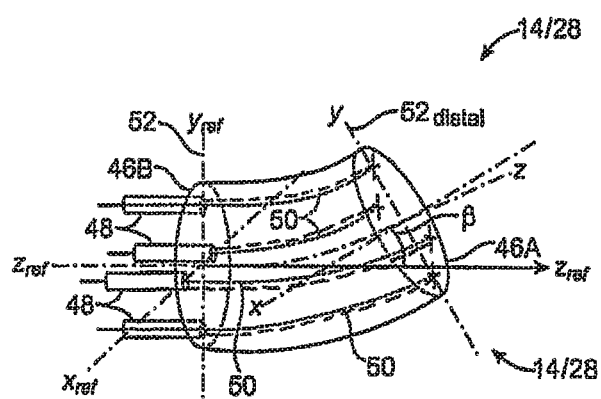
Figure 3C:
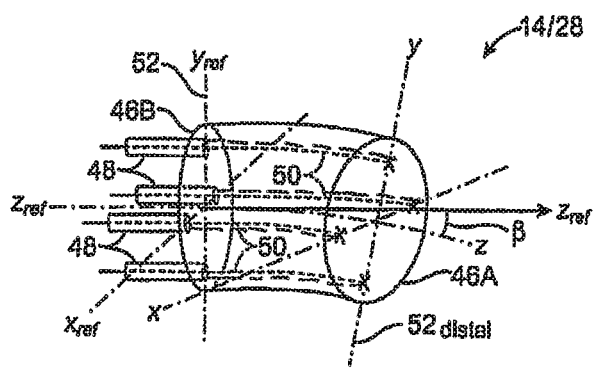

Referring now to FIG. 3A-C a schematic diagram of either steerable distal portion 14 or segments 28 is provided for discussion purposes and to explain a preferred system and method for articulating steerable distal portion 14 or segments 28. The skilled artisan will recognize that the system and method for articulation is the same for both steerable distal portion 14 and segments 28 of automatically controlled proximal portion 16. Therefore, the system and method for articulation will be described referring only to segments 28, with the recognition that the description also applies equally to steerable distal portion 14. It is noted that details relating to links 46, joints 47 and the interconnections of the links have been eliminated from this figure for the sake of clarity.

FIG. 3A shows a three-dimensional view of segment 28 in its substantially straight configuration. The most distal link 46A and most proximal link 46B are depicted as circles. Bowden cables extend down the length of elongate body 12 (not shown in FIGS. 3A-C) and comprise coil pipes 48 and tendons 50. The proximal end of the Bowden-type cable is coupled to an actuator (not shown) and the distal end is coupled to the segment for which it controls articulation. Coil pipes 48 house tendons 50 (i.e. a Bowden-type cable) along the length of elongate body 12 (not shown in FIGS. 3A-C) and coil pipes 48 are fixed at the proximal end of segment 28. Tendons 50 extend out of coil pipes 48 at the proximal end of segment 28 along the length of segment 28, and are mechanically attached to the distal portion of segment 28. It will be appreciated that the distal end of tendons 50 need only be attached to the segment (or link if a segment is made up of only one link) being articulated by that tendon 50 at a location required to transfer the actuated force to that segment to effect articulation; the distal portion of the segment is provided by way of explanation and example, and not by way of limitation. In the variation depicted in FIG. 3A-C four tendons 50 are depicted to articulate segment 28, but more or fewer may be used. The coil pipe/tendon combination, or Bowden cables, can be used to apply force to articulate segments 28 and can be actuated remotely to deliver forces as desired to articulate segments 28. In this manner, actuation of one or more tendons 50 causes segment 28 to articulate. In the embodiment depicted, links 46 have joints 47 alternating by 90 degrees (see FIGS. 2 and 4). Thus, an assembly of multiple links 46 is able to move in many directions, limited only by the number of actuated joints. As will be appreciated by the skilled artisan, tendons 50 can be made from a variety of materials, which is primarily dictated by the purpose for which the endoscope will be used. Without limitation tendons 50 can be made from stainless steel, titanium, nitinol, ultra high molecular weight polyethylene, the latter of which is preferred, or any other suitable material known to the skilled artisan.

In the variation depicted in FIG. 3A-C, four tendons 50 are used to articulate segment 28, although more or fewer tendons could be used, as will be appreciated by the skilled artisan. Four tendons can reliably articulate segment 28 in many directions. Tendons 50 are attached at the most distal link 46A, for the purposes of this discussion but not by way of limitation, close to the edge spaced equally apart at 12, 3, 6, and 9 O'clock. It will also be noted that an equal angle approximation has been made with this figure, that is the amount of bend is equally distributed to each of the joints of a segment.

FIG. 3B-C show segment 28 articulated by independently pulling or slacking each of the four tendons 50. For example, referring to FIG. 3B, pulling on tendon 50 at the 12 O'clock position and easing tension on tendon 50 at the 6 O'clock position causes steerable distal portion 28 to articulate in the positive y-direction with respect to the z-y-x reference frame 52. It is noted that the most distal z-y-x coordinate frame $52_{distal}$ rotates with respect to the z-y-x reference frame 52 and that β is the degree of overall articulation of segment 28. In this situation 13 is only along the positive y-axis, up, because only tendon 50 at the 12 O'clock position was pulled while easing tension or giving slack to tendon 50 at 6 O'clock. The tendons 50 at 3- and 9 O'clock were left substantially static in this example, and, thus, had approximately no or little affect on articulation of segment 28. The reverse situation (not depicted), pulling on tendon 50 at the 6 O'clock position and slacking or easing the tension on tendon 50 at the 12 O'clock position results in articulation of segment 28 in the negative y-direction, or down. Referring to FIG. 3C the same logic applies to articulate segment 28 in the positive x-direction (right) or a negative x-direction (left, not shown). Segment 28 can be articulated in any direction by applying varying tensions to the tendons off axis, e.g., applying tension to the tendons at 12 O'clock and 3 O'clock results in an articulation up and to the left.

Referring now to FIG. 4, links 46 may be control rings to provide the structure needed to construct steerable distal portion 14 and segments 28. Vertebrae-type control rings 54 have two pairs of joints or hinges 58A and 58B; the first pair 58A projecting perpendicularly from a first face of the vertebra and a second pair 58B, located 90 degrees around the circumference from the first pair, projecting perpendicularly away from the face of the vertebra on a second face of the vertebra opposite to the first face. Hinges 58A and 58B are tab-shaped, however other shapes may also be used.

Figure 4A:
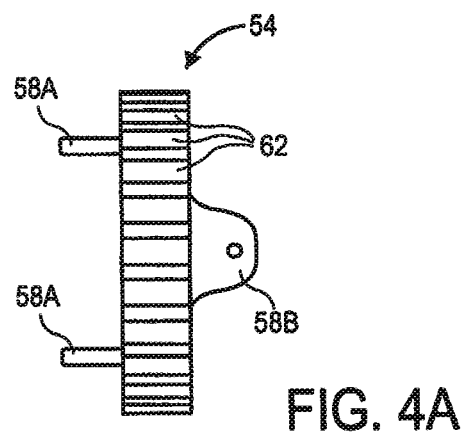
FIGS. 4A, 4B, 4C and 4D illustrate various views of a vertebra style control ring.
Figure 4B:
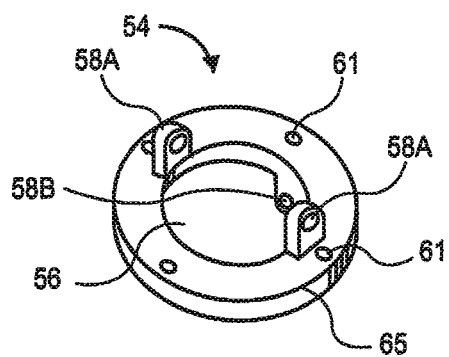
Figure 4C:
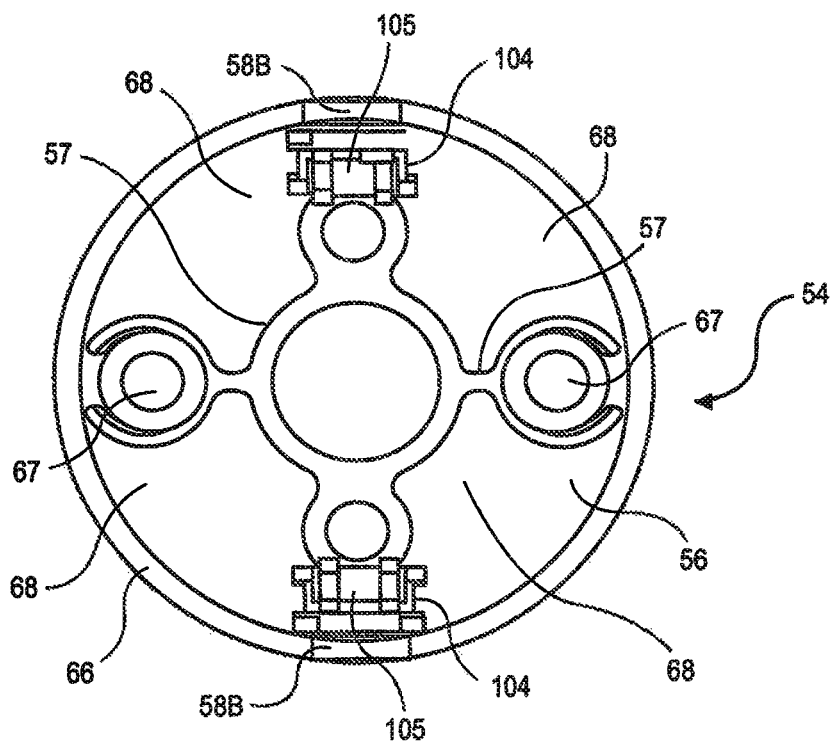
Figure 4D:
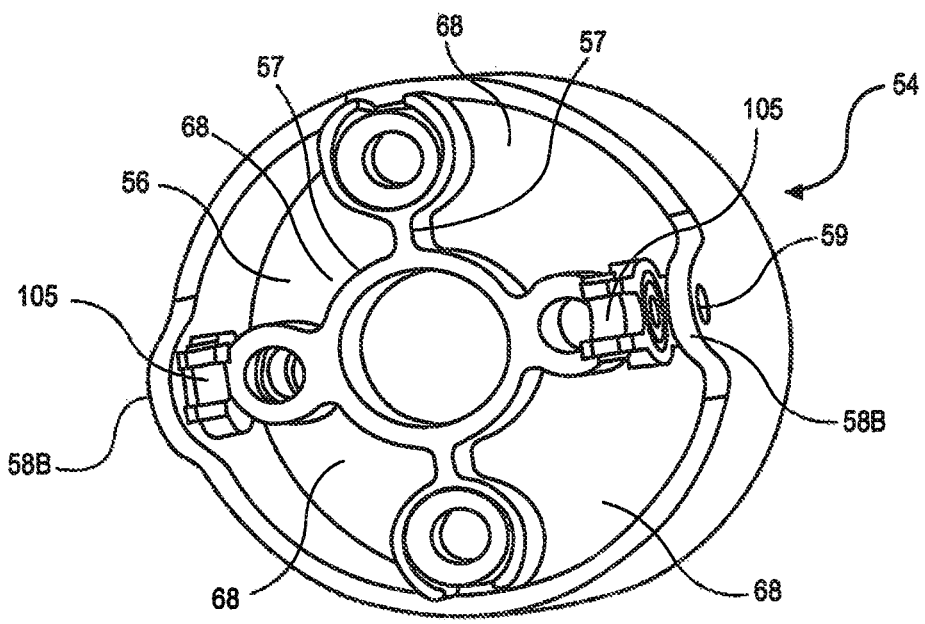

FIG. 4C-D shows vertebra-type control ring 54 in sectional and perspective views. Control ring 54 comprises body 66, which is hingedly coupled to inner cross bar member 57 at joints 59. Joints 59 are the same joints at which a second link (although not shown) adjacent and proximal to link 54 is hingedly coupled to link 54. Inner cross bar member 57 is therefore hingedly coupled to two links at joints 59, and can be thought of as being axially disposed "between" the two links. Cross bar member 57 can also be fixed relative to one or both of the adjacent links. The exemplary inner cross bar member 57 comprises force modifying elements 104 or purchase which each interact with a tendon 50 (not shown in FIGS. 4D and 4E) to increase the amount of force applied to the articulatable segment when an actuation/tensioning force is applied to the tendon. Bar 105 is provided as a tie-anchor for a tendon coming back down the segment from the purchase.

The skilled artisan will appreciate that coil pipes 48 by-passing a vertebrae via quadrants 68 will define an approximately cylindrical coil pipe containment space roughly defined by the outer diameter of vertebrae-type control ring 64. Management of the coil pipes is more thoroughly discussed in co-assigned U.S. patent application Ser. No. 11/871,104 previously incorporated herein by reference. This space is loosely defined by the grouped coil pipes as they pass through and between the vertebrae. As described more thoroughly below, it is possible and preferred to have intermediate vertebra-type control rings without coil pipe bypassing spaces and therefore without crossbars 57. In either construction, central aperture 56 or 56' of the control rings collectively forms a lumen (not shown) through which channels and cables necessary or desired for the endoscope function pass, as well as coil pipes and tendons by-passing that particular segment.

Figure 5:
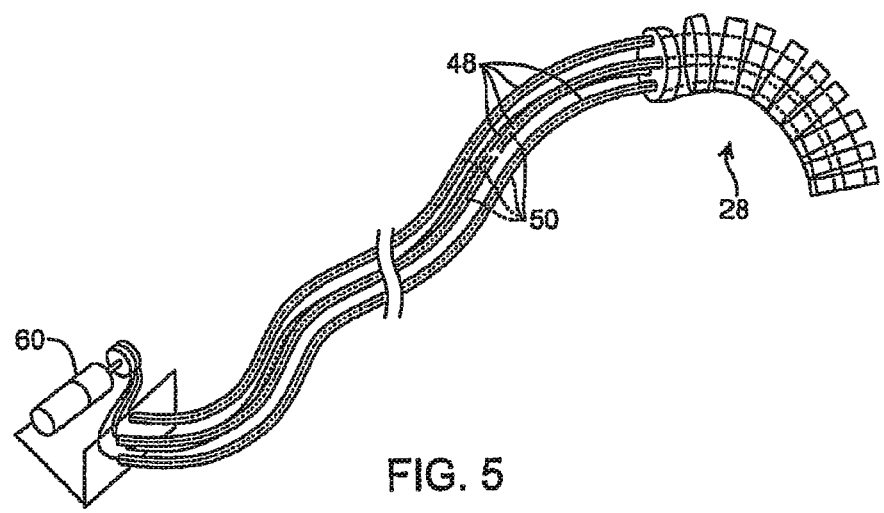
FIG. 5 illustrates a segment and its associated control cables or tendons and a drive motor used to drive one of the tendons to control the movement of the segment.

Referring to FIG. 5, coil pipes 48 are fixed at their distal and proximal ends between actuators 60 and the proximal end of segment 28 under control by those actuators. FIG. 5 shows only one segment 28 (which, as discussed, could also be steerable distal portion 14), and, for clarity, the other parts of a complete endoscope have been omitted from FIG. 5. When tendons 50 are placed under tension, the force is transferred across the length of segment 28; coil pipes 48 provide the opposite force at the proximal end of the segment being articulated in order to cause the articulation. This force is, primarily, axial loading transferred along the length of the coil pipe where it is fixed between the actuator and the proximal end of the segment being articulated. A preferred embodiment of the present invention utilizes one actuator per tendon, and utilizes four tendons per segment, as described above, although only one actuator 60 is depicted for clarity. Details relating to actuator 60 and connecting actuator 60 to tendons 50 are described in U.S. patent application Ser. No. 10/988,212, previously incorporated by reference.

The skilled artisan will appreciate that articulation of multiple segments 28 along the length of elongate body 12 will require that many coil pipes 50 extend down the length of elongate body 12 and through coil pipe by-passing spaces, with the number decreasing by four coil pipes (in this example) at the proximal end of each segment. Thus, a 17 segmented elongate body (16 segments 28 and 1 tip 14) requires 68 coil pipes going into the proximal end of elongate body 12, which decreases by four coil pipes for each distally adjacent segment 28 (assuming one uses four tendon/coil pipes combinations per segment as in the present example). It also requires the actuation or tensioning of 68 tendons, with four tendons terminating at the distal end of each segment. This requires 68 actuators in this embodiment, one actuator per tendon 50.

The skilled artisan will also appreciate that there is not a one to one correspondence between the force applied by actuators 60 at the proximal end of tendons 50 and the force realized at the distal end of tendons 50 to articulate segment 28. Friction between tendons 50 and coil pipes 48 results in frictional losses along the length of the coil pipe while applying tension to articulate a segment or the tip. Articulation of segments 28 and steerable distal portion 14 results in further losses and inefficiencies for many reasons. For example, and without limitation, when elongate body 12 articulates (for example at the Sigmoid colon during a colonoscopy procedure or when retroflexing or navigating upon exiting the stomach in a NOTES procedure), coil pipes 48 must move longitudinally along elongate body 12 to either "gain" or "lose" length depending whether coil pipes 48 are on the inner or outer portion of the bend created by the articulation. As described above, an embodiment of the present invention provides quadrants 68 or coil pipe by-passing spaces 62 that permit the passage of coil pipes 48 along elongate body 12 until they reach the proximal portion of the segment they control. The "gain" or "loss" of coil pipe length requires coil pipes 48 to slide up and down elongate body 12 and within quadrants 68 or coil pipe by-passing spaces 62 creating further frictional losses by virtue of friction between the coil pipes and/or between the coil pipes and the vertebra. There is also the additional friction created between a coil pipe and a tendon by virtue of the bend. Additionally, but related, elongate body 12 may enter more than one tortuous bend simultaneously. This may occur when going through a tortuous path such as the colon or when navigating the scope in open space (e.g., within the peritoneal cavity) to perform NOTES procedures. In one mode of operation, as described more thoroughly in U.S. patent application Ser. No. 11/019,963, previously incorporated herein by reference, electronic motion controller 30 causes adjacent segments to adopt the shape of the segment or steerable distal portion immediately preceding it. As described above, coil pipes 48 need to slide along elongate body 12 to accommodate the "gain" or "loss" of coil pipe length resulting from the articulation of elongate body 12. In order to localize this "gain" or "loss" the coil pipes are spiraled. In effect, it is believed, spiraling localizing the sliding of the coil pipes to the segment, thereby preventing binding of the coil pipes and catastrophic failure. This is described in further detail in co-pending, co-assigned U.S. patent application Ser. No. 11/871,104 titled System for Managing Bowden Cables in Articulating Instruments.

Performing procedures within a patient, such as in natural orifice transluminal endoscopic surgical procedures, may require a stable, semi-rigid platform from which to perform the procedure. Lockable tubes in the prior art have the surface of one ring contacting the surface of an adjacent ring. Compression of the adjacent rings in these prior art lockable tubes increases the friction between the adjacent rings causing them to resist articulation relative to each other.

In contrast to conventional locking approaches, embodiments of the inventions described herein provide additional frictional surfaces or in some embodiments multiplied frictional surfaces between articulating components. It is believed that the additional surfaces increase the frictional surface acting on the instrument. The additional frictional force in turn increases the braking or locking force applied to the instrument. Various embodiments of the present invention provide mechanisms by which the user can selectively rigidize all or a portion of the elongate body through the use of multiple surfaces placed between articulating segments or individual links or vertebra. In addition, while the braking assemblies described herein provide multiplied friction and lock force, they remain capable of articulation when not engaged. In some embodiments, the brake assembly includes the hinge or portion of a hinge or joint used for the articulation of the segmented instrument.

In one aspect, there is provided a segmented instrument having a plurality of links and at least one lockable and articulatable joint positioned to connect a pair of adjacent links in the plurality of links. In addition, the at least one lockable and articulatable joint being adapted and configured to increase the number of frictional surfaces available between the pair of adjacent links. As described above, cables and coil pipes take up a large amount of space along the elongate body. In one aspect, the brake assembly lies on or in the exterior surface of the segment, hinge or vertebra in order to keep the interior portions of the instrument free.

In one embodiment of the present invention, there is a segmented instrument having braking capabilities. The instrument includes an elongate body having a plurality of links. The instrument may be configured as any of a wide variety of surgical devices. For example, the instrument may be an endoscope or other controllable instrument as described above or it may be a guide used to direct the movement or placement of another instrument including another segmented instrument. A hinge connects a pair of adjacent links in the plurality of links. There is a brake assembly coupled to each link in the pair of adjacent links. The brake assembly is positioned to span the distance between the pair of adjacent links.

The skilled artisan will readily recognize appropriate materials from which to make components in a brake assembly. The desired properties of the materials used in a brake assembly include lubricity between layers when the brake is not actuated (e.g., braking force is not applied or no vacuum is pulled) and sufficient friction to bind the components or brake assembly when the brake is actuated (e.g., the braking force is applied or a vacuum is pulled). Another useful property is that the brake assembly has the flexibility to bend when a joint is articulated. Exemplary materials for use in brake assembly components include, without limitation, aluminum, carbon fiber, and various plastics such as and without limitation Teflon®.

The brake assembly may be on all or only some of the links, vertebra or segments of an instrument. The brake assembly or multiple brake assemblies may be placed in isolated or only specific portions of the instrument. Numerous actuation mechanisms may be used to engage the brake assembly or assemblies. In one aspect, the brake assemblies are activated by pulling a cable running through or along the instrument. In another alternative form of activation, the interior of the scope (a normally sealed environment) is pumped down so that the interior is under vacuum. The action of the skin of the instrument being pulled in by the vacuum may be used to actuate a braking mechanism. In addition, the brake assemblies may be activated serially or simultaneously or in any order depending upon circumstances in use. The brake assembly or assemblies may be provided only in a distal portion of the links in the plurality of links. Alternatively, the brake assembly is provided only in a proximal portion of the links in the plurality of links. In still another alternative, the brake assembly is provided only in a middle portion of the links in the plurality of links.

The movement of the pair of adjacent links about the hinge is prevented when the brake assembly is engaged. In one aspect, the brake assembly is provided only between a portion of the links in the plurality of links. There are configurations of the braking assembly where one or more are placed wherein the actuation of the brake assembly removes one degree of freedom from a portion of the instrument. In other aspects, a plurality of brake assemblies are coupled to the instrument. In this example, the actuation of the plurality of brake assemblies substantially locks the shape of instrument by locking substantially all of the plurality of links in the instrument. In an alternative configuration, the plurality of brake assemblies are coupled to the instrument wherein actuation of the plurality of brake assemblies substantially removes one degree of freedom from the movement of the segmented instrument.

In addition, the brake assembly is adapted and configured to complement the operation of the hinge so that the hinge remains articulatable when the brake assembly is not actuated or engaged. The brake assembly is adapted and configured to increase the number of frictional surfaces between the pair of adjacent links. In some embodiments, there is a recessed portion on the surface of the each of links in the pair of adjacent links sized and shaped to conform to the size and shape of a portion of a component in the brake assembly. The size and shape of the recessed portion will vary with the particular brake assembly design implemented. By way of example, the recessed portion on the surface of the each of links in the pair of adjacent links has a generally rectangular shape or, alternatively, a generally arcurate shape.

The brake assembly is spaced apart from the at least one hinge. In one aspect, the brake assembly is spaced apart about 90 degrees about the circumference of the link from the at least one hinge. Practical limitations of the actual design of a specific instrument may alter the location of the braking mechanism. The spacing may be as close as practical to 90 degrees from the hinge location.

In some embodiments, the brake assembly may also include a plurality of complementary shaped components. The complementary shaped components may have surfaces adapted and configured to provide sliding motion when links move about the hinge. The complementary shaped components may come in virtually any shape and orientation that allow sliding, relative movement. In one example, the plurality of complementary shaped components may be provided by a plurality of interwoven slats. This is one example where the complementary surfaces are generally flat. In still another example, the complementary surfaces are generally arcurate. In still another aspect, a complementary shaped component positioned adjacent one link in the pair of links moves along with the movement of the other of the links in the pair of links.

Figure 6:
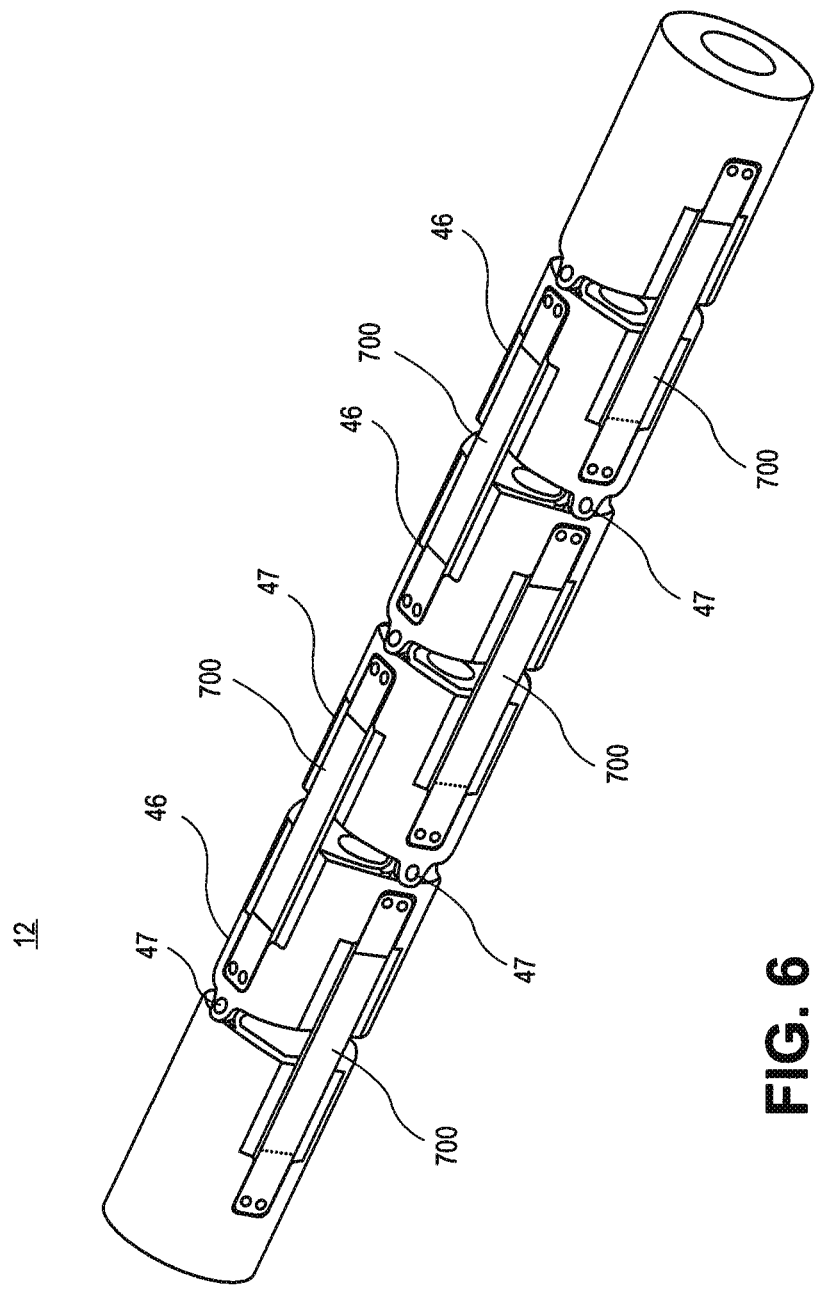
FIGS. 6, 7 and 8 illustrate various embodiments of a segmented instrument having an embodiment of a vacuum brake assembly.
Figure 7:
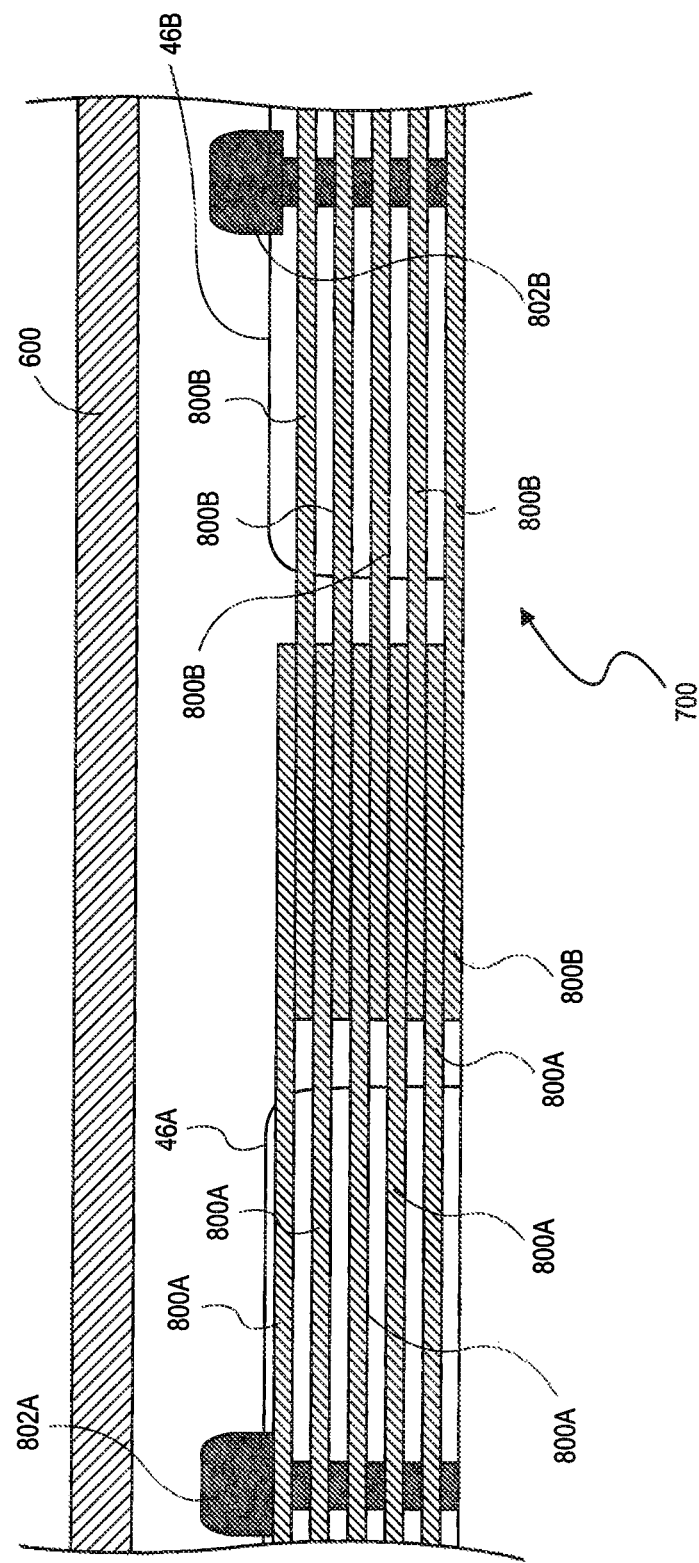
Figure 8:
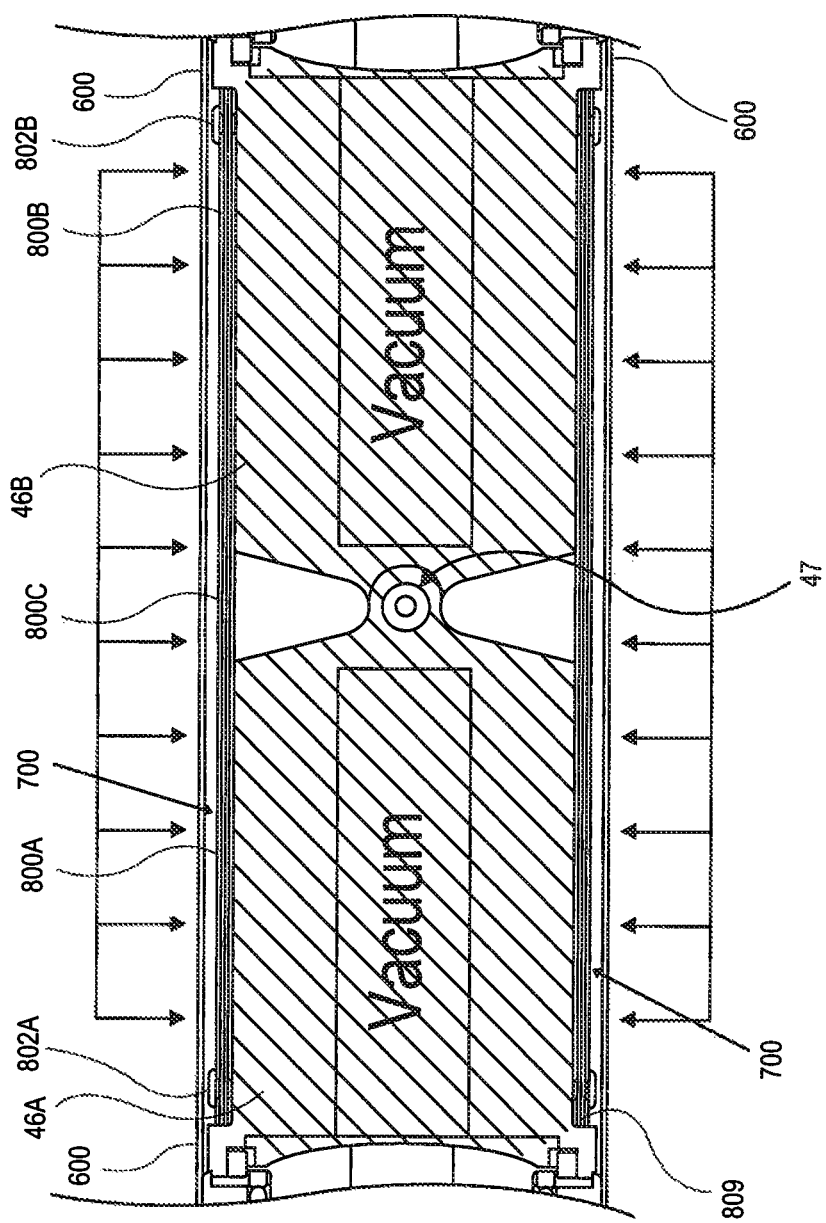

One embodiment of the present invention uses a vacuum mechanism to lock or rigidize the elongate body. FIGS. 6, 7 and 8 will now be used to explain the operation of one embodiment of an instrument having braking or locking capabilities. FIG. 6 is an isometric view of an instrument with an embodiment of a brake assembly 700. FIG. 7 is an enlarged section view of a brake assembly 700 in FIG. 6. FIG. 8 illustrates a section view of two links and the forces applied to the brake assembly by the instrument skin 600.

As best seen in FIGS. 7 and 8 the instrument elongate body 12 has skin 600 over its outside. Skin 600 is preferably made from some smooth, elastic and durable material in order to prevent trauma to the patient as elongate body 12 is moved about within the patient.

FIG. 6 is an isometric view of a portion of an instrument having six links 46. This view shows the instrument without skin 600 so that the position of the brake assembly 700 may be seen in relation to the hinge 47. In this embodiment, a brake assembly 700 is attached between adjacent links 46. In the illustrative embodiment of FIG. 6, the brake assembly 700 is located approximately ninety degrees about the circumference of link 46 from joint 47. The brake assemblies 700, when engaged, substantially prevent articulation of link 46 about its joint 47. Thus, when a brake assembly 700 is engaged the degree of freedom provided in each link is substantially removed. When a plurality of brake assemblies acts together, they substantially rigidize or lock the elongate body 12 in the shape existing when the brake assembly is actuated.

FIG. 7 illustrates a partial section view of an embodiment of a brake assembly 700 shown in FIG. 6. Referring to FIG. 7, brake assembly 700, in one embodiment, includes interwoven slats or layers 800. Interwoven slats or layers 800 slide next to and between each other and are secured on either side of hinged links 46 by pins 802. Slats or layers 800A are attached to link 46A using pin 802A. Slats or layers 800B are attached to link 46B using pin 802B. The location of pins 802A, B and the length of the slats or layers 800A, 800B are selected so that the overlapping region 800C exists throughout the range of motion for the hinge 47 (not shown) associated with links 46A, 46B. By selecting the proper length of slats 800A, 800B with a sufficient overlapping region 800C, the brake assembly 700 can engage irrespective of the relative position of links 46A, 46B. This sliding arrangement of the slats/layers 800A, 800B which permits articulation of joint 47 when brake assembly 700 is not engaged.

In this embodiment, a vacuum is pulled within elongate body 12, and the pressure difference causes skin 600 to apply a force against links 46 and against brake assembly 700, as depicted by arrows in FIG. 8. This force acts against the brake assembly 700 causing the interwoven slats or layers 800A, 800B to engage by pressing layers 800A, 800B together in the overlapping region 800C as well as against each other and the surface of the links 46A, 46B. The increase of friction between layers 800A, 800B upon application of the force causes brake assembly 700 to engage, thereby inhibiting articulation of the joint across which the brake assembly spans. Release of the vacuum removes the force applied to brake assembly 700 by the skin 600, thereby permitting sliding movement again between the slats 800A, 800B and articulation of the joints and the elongate body.

Also shown in FIG. 8 is the recessed portion 809. The recessed portion 809 is positioned on the surface of the each of links 47 in the pair of adjacent links. The recessed portion 809 is sized and shaped to conform to the size and shape of a portion of a component in the brake assembly. In this illustrative example, the size and shape of the recessed portion 809 corresponds to the size of the slats 800A, 800B and is generally rectangular like the slats 800A, 800B. The size and shape of the recess 809 will vary with the specific brake assembly or technique being utilized. In an alternative embodiment, the recessed portion on the surface of the each of links in the pair of adjacent links may have a generally arcurate shape, a curved shape, an irregular shape or a compound shape.

In alternative embodiments of the present invention, one or more cables (preferably different from the actuation tendons) running along or through the edges of links 46 of elongate body 12. Each joint of each vertebrae or link 46 has brake assembly or articulating lockable brake assembly as described herein. In one aspect, the various alternative brake assemblies have multiple surfaces that slide next to each other about a pivot point when force is not applied, thereby permitting articulation of the link. One aspect of the embodiments of the brake assemblies described herein that allows the surfaces to effectively multiply the friction at the joint is that the sliding plates between the rings can move freely separate along the central axis of the rings, but cannot rotate relative to either the upper or lower ring depending on which one they are contiguous with. In other words, when load is removed from the joints, the components are allowed to separate, facilitating articulation. When load is applied to the joints, the surfaces compress and friction is generated at the interfaces, resisting articulation. This design is not limited to just three interfaces as depicted in some embodiments described herein. For a given load, by increasing the number of frictional interfaces increases the resistance to articulation.

The multiple surfaces of the brake assemblies bind when load is placed on the links, in this embodiment by applying tension to the cables. The applied tension compresses the links together, which in turn compresses multiple surfaces together preventing the links from articulating, and, thereby, rigidizing elongate body 12. This design is not limited to just the number of interfaces depicted. For a given load, increasing the number of frictional interfaces increases the resistance to articulation.

In some aspects, one or more brake assembly components may be part of and contiguous with a link structure. In other configurations, one or more brake assembly components may be slidingly pinned into a link structure such that it can have limited movement longitudinally up and down relative to a link structure. In this regard, it may in essence be part of a link structure as well. Other brake assembly components may be attached to a link structure 46 by pivot arms and such that these surfaces may articulate along upper arched surfaces or other complementary surfaces of 958 of a link structure 46. In some embodiments, one can see each link structure 46 contributes two surfaces to either side of a brake assembly, for a total of three contact surfaces for each joint. In addition and where needed, holes are provided in link structure 46 for the passage of cables 900 used to articulate the links and other cables to compress the multiple surfaces together, thereby locking link structures relative to each other. When not compressed, the surfaces described above and in the various brake assembly embodiments will slide relative to each other to permit bending or articulation of the controllable instrument (e.g. guide tube or segmented controllable instrument) made from the ring structures and brake assemblies.

The components of the brake assembly 900 are compressed via a cable that runs through links 46, as previously described. Tension in the cables is generated using a lead screw with a balance bar to distribute the load evenly between joints. Any method that generates a compressive load is acceptable given that the loads do not act to articulate the joint, but rather to compress it. The compressive load should act directly through the pivot point of the joint if possible.

It is further noted that articulation of each link has one degree of freedom, as described above. Preferably, the direction of the degree of freedom alternates for adjacent links and is orthogonal for adjacent links. In this manner segments made of multiple links can be articulated in multiple directions using tendons and actuators, as described above. In this embodiment the articulating elongate body can be selectively rigidized by actuating the cables. In an alternative embodiment, the multiplying surfaces can be used to selectively rigidize an over tube, which is used to guide an instrument. The instrument can either be a passive endoscope, such as that made by Olympus, or a fully controlled articulating scope, such as that described above and in development by NeoGuide Systems, Inc.

Figure 9:
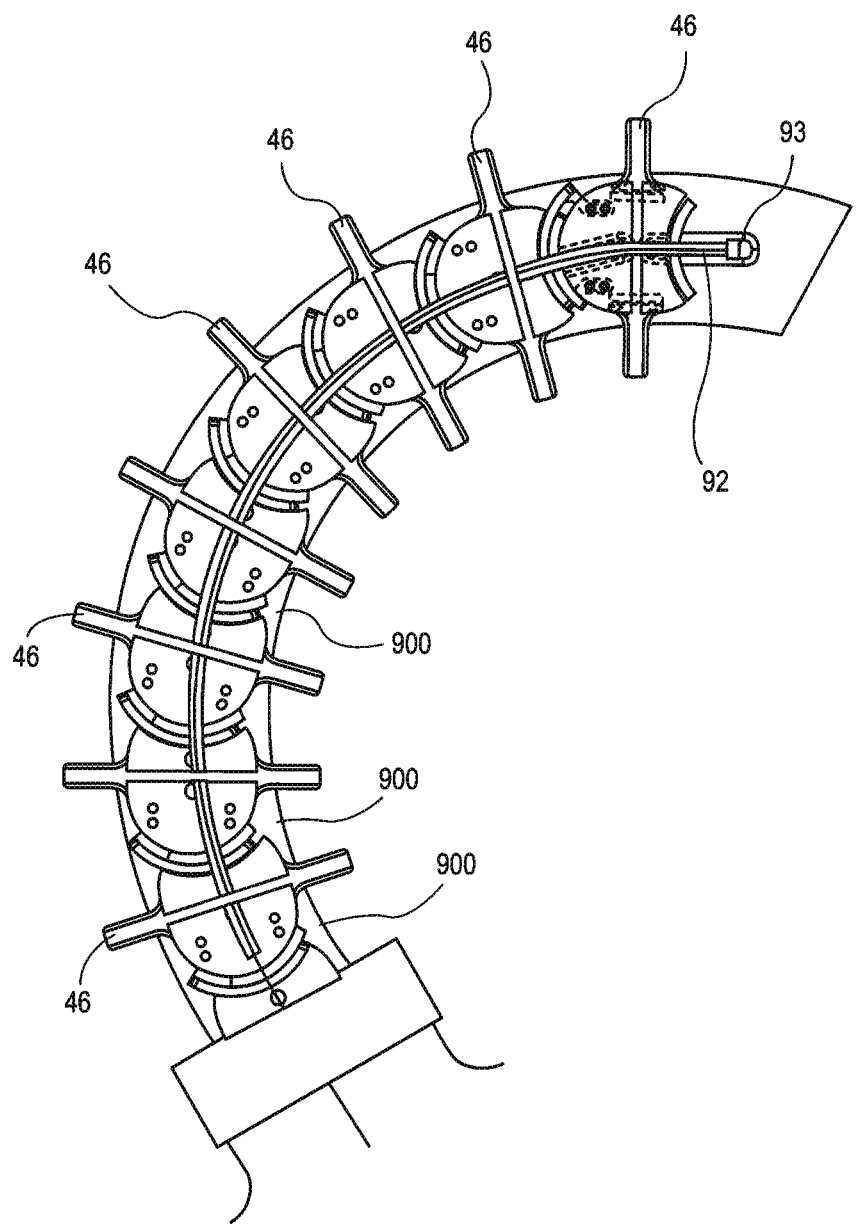
FIGS. 9, 10, 11, and 12 illustrate various views of an embodiment of a controllable instrument having braking capabilities.

Turning now to FIGS. 9-12 that illustrate various views of another embodiment of a segmented instrument having braking capabilities. As shown in FIG. 9, there is an illustration of an elongate body having a plurality of links 46. There is a hinge connecting a pair of adjacent links in the plurality of links and a brake assembly 900 coupled to each link in the pair of adjacent links. The brake assembly 900 is also positioned to span the distance between the pair of adjacent links 46. A cable 92 extends through the plurality of brake assemblies 900 to a stopper 93 on the distal end. When the cable 92 is drawn proximally either manually by a user or by a motor or other drive system under the control of a computer controller, the stopper 93 engages with the components of the brake assembly 900 to engage and lock the position of the segmented instrument.

Figure 10:
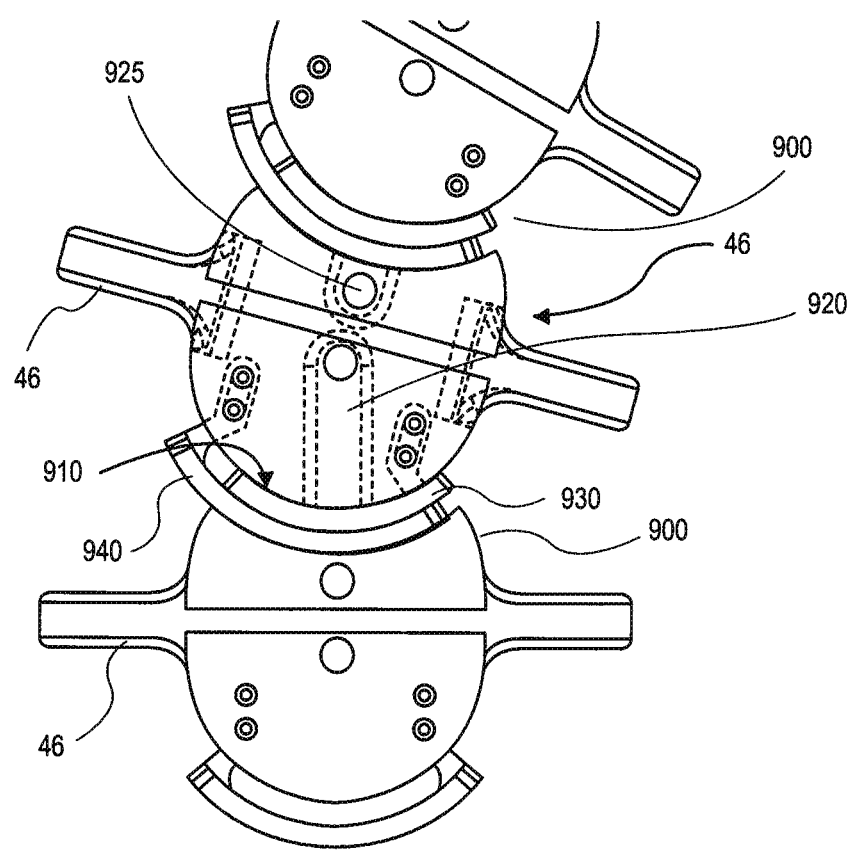
Figure 11:
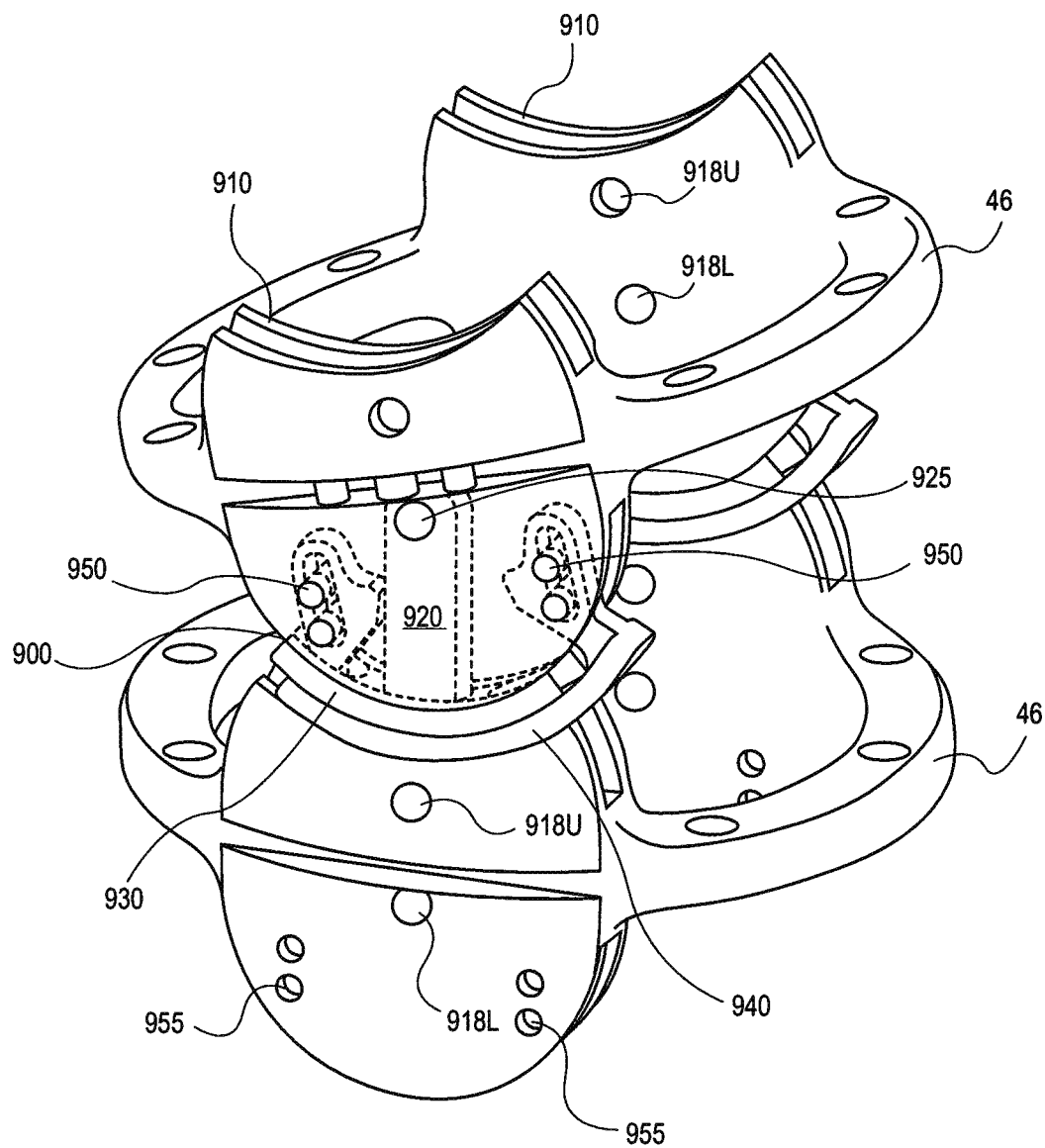
Figure 12:
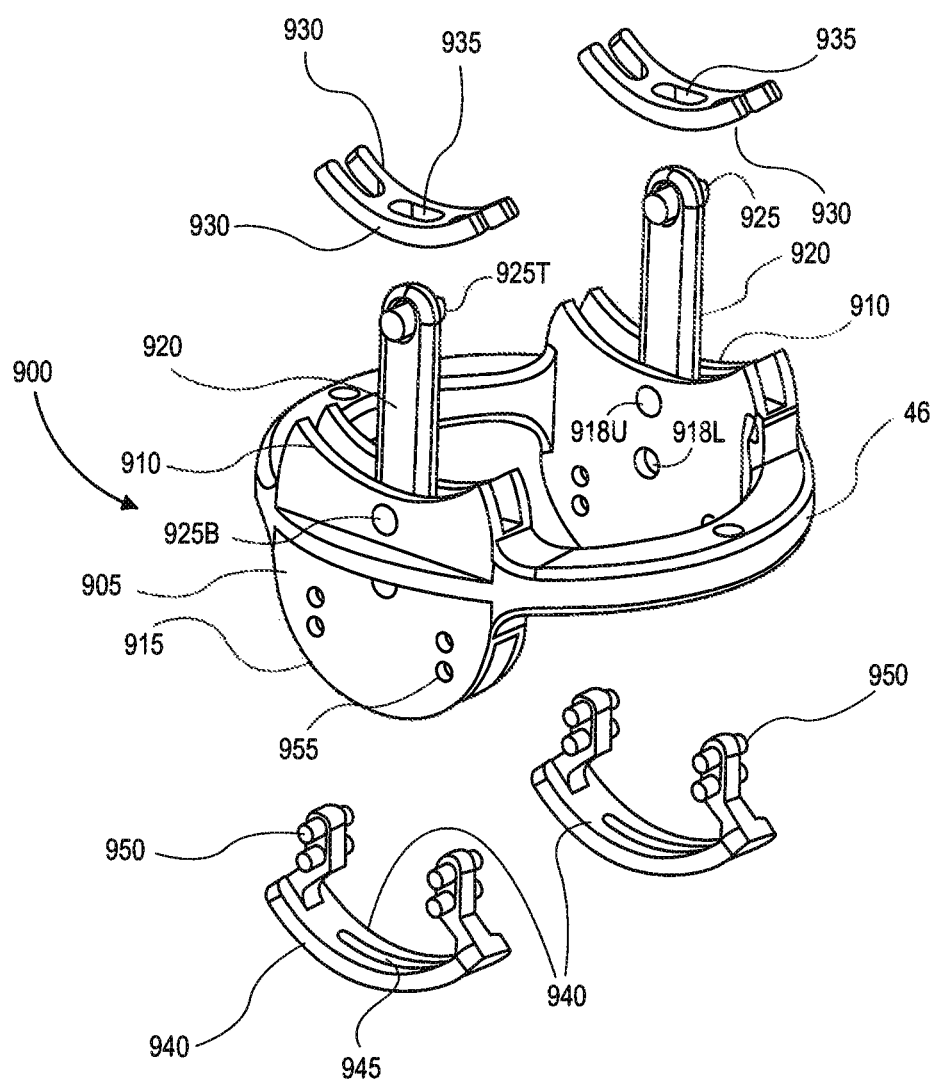

The internal components of the brake assembly 900 are best seen in the views provided by FIGS. 10, 11 and 12. FIGS. 10 and 11 provide side and isometric views, respectively, of at least two links coupled together by the brake assembly 900. The specific components of the brake assembly will now be described with reference to the exploded view of FIG. 12.

FIG. 12 illustrates an exploded view of the components of an exemplary brake assembly 900. The link 46 includes a brake assembly base 905 having shaped upper complementary surface 910 and lower shaped complementary surface 915. Apertures 918U, 918L are formed in the base are sized and positioned to receive the common pins 925 provided by arms 920. Apertures 955 are sized and positioned to receive pins 950 of the link slider 940. Arm 920 includes common pins 925T on one end and pins 925B on the other. The pins 925T couple to apertures 918L and the pins 925B couple to the apertures 918U. The common pins and the arms provide the hinge between the links and allow for relative movement between adjacent links. The arms 920 shown in the view of FIG. 12 illustrate the connection between pins 918U into aperture 918U of the link 46 shown in the figure.

The arm 920 also passes through the arm slider 930 and link slider 940. Arm slider 930 includes an aperture 935 for the arm 920. Link slider 940 includes an aperture 945 for the arm 935. The arm slider 930 is shaped to provide complementary surfaces for both the base upper surface 910 to one side and the base lower surface 915 to the other. As shown in the views of FIGS. 10 and 11, when the brake assembly 900 is in use, the arm slider 930 is in sliding relation and has complementary shape to slide between the link upper and lower surfaces 910, 915. The arm slider moves independent of the links 46 and provides additional friction surfaces to lock the relative position of the links 46. The link slider 940 also provides additional friction lock surfaces. In contrast to the arm slider 930, the link slider 940 is pinned to the link using the pins 950 and apertures 955. As such the link slider moves with the link 46. The link slider 940 has complementary shaped surfaces that provide the increased number of friction surfaces between the base lower surface 915 and the arm slider 930 and the base upper surface 910.

As best seen in the assembled views of FIGS. 10 and 11, both the arm slider 930 and the link slider 940 have apertures adapted and configured to fit around and permit passage of the arm 920. In this embodiment of the brake assembly 900, the complementary surfaces and increased friction lock surfaces are, from the base lower surface 915 of the upper link 46: lower base surface 915 contacts the upper surface of the arm slider 930, the lower surface of the arm slider 930 contacts the upper surface of the link slider 940 and the lower surface of the link slider 940 contacts the upper base surface 910 of the lower link 46. Each of the above surfaces has a complementary shape that allows sliding movement and articulation of the links 46 when the brake 900 is not engaged. When engaged, the surfaces and components above act in concert to lock the relative position of the links 46.

Figure 13:
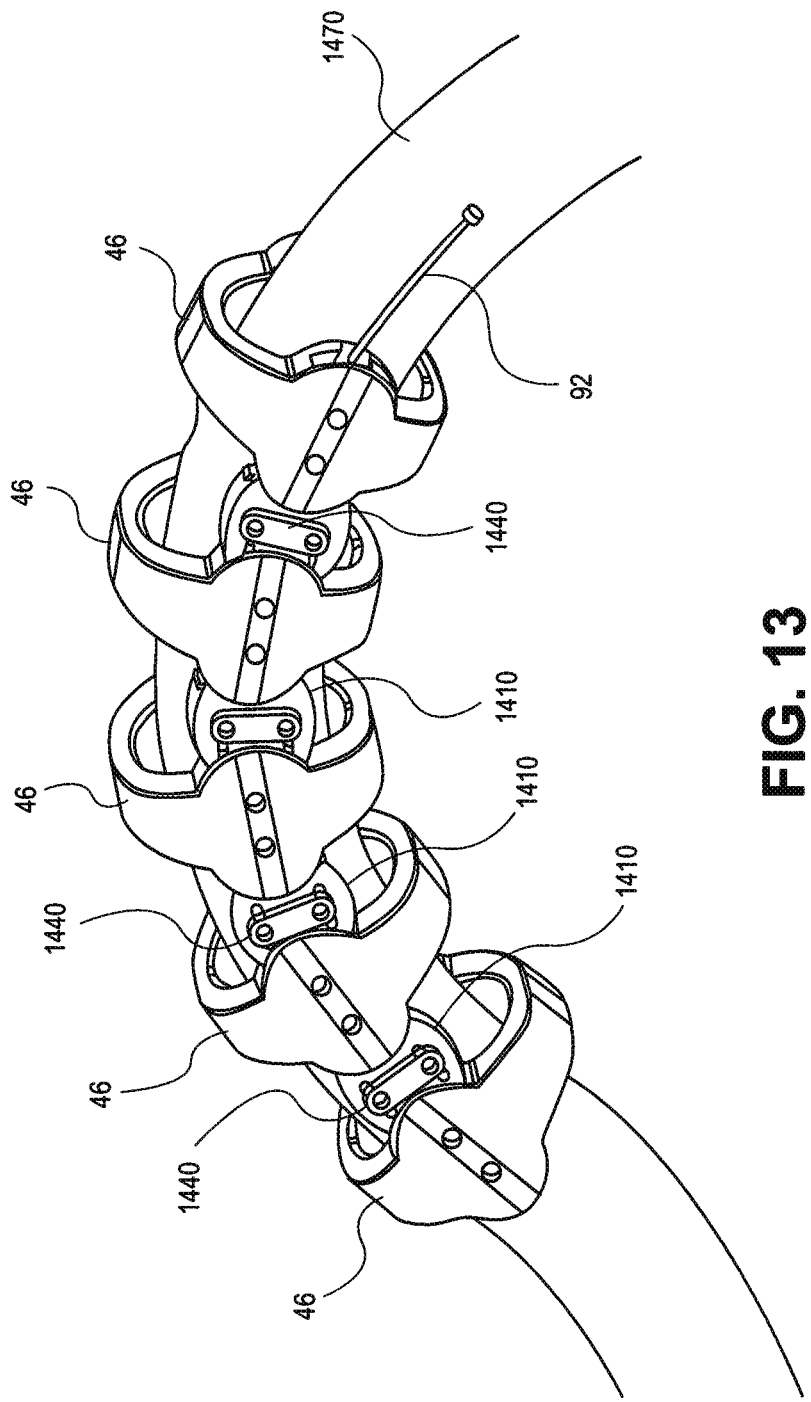
FIGS. 13, 14, 15A, 15B and 16 illustrate various views of another embodiment of a controllable instrument having braking capabilities.
Figure 14:
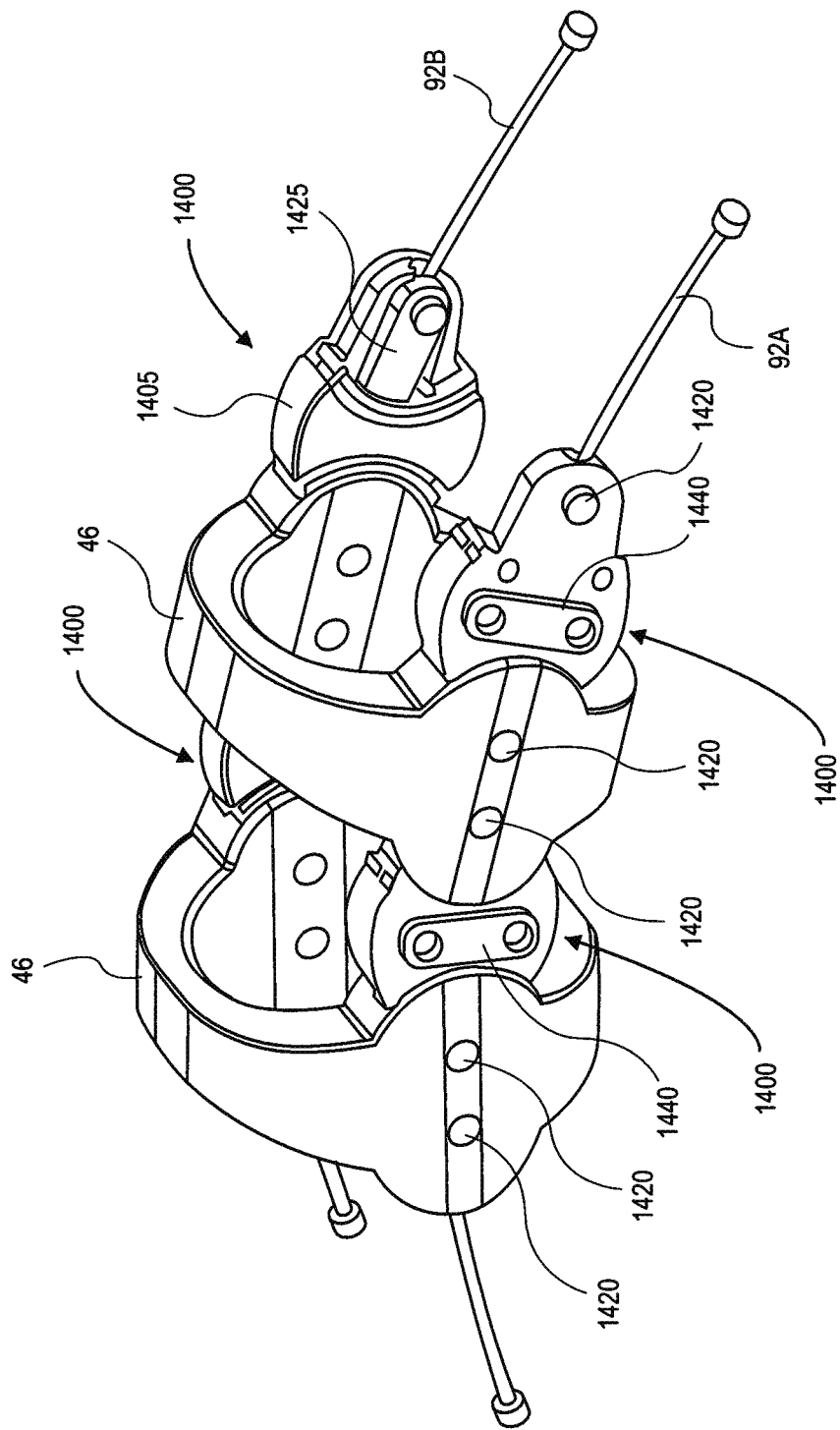
Figure 15A:
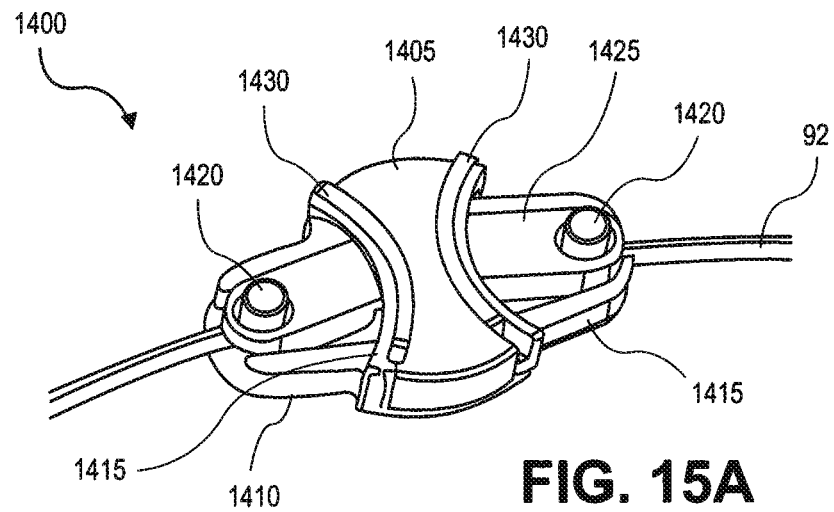
Figure 15B:
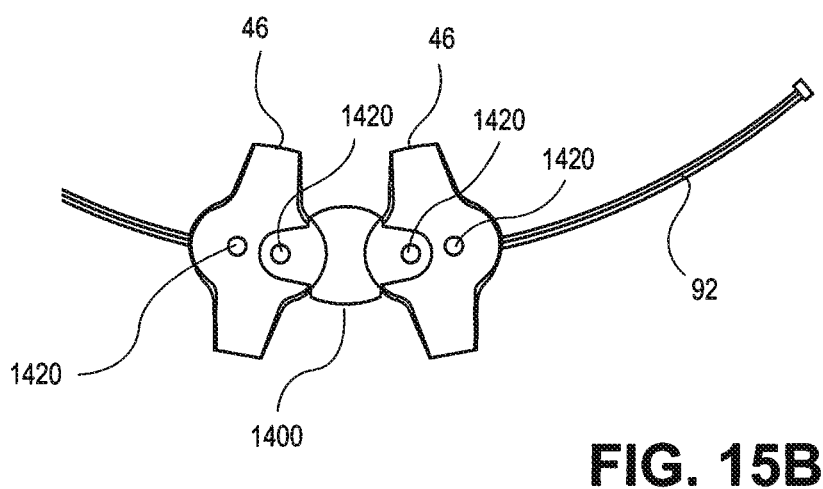
Figure 16:
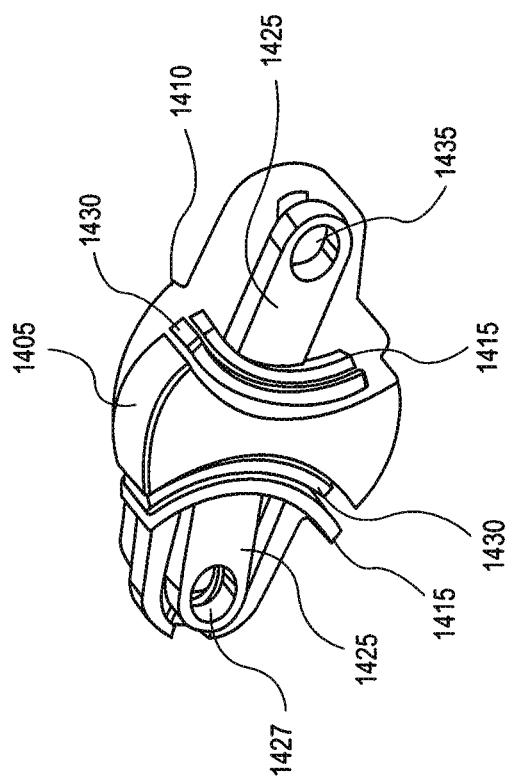

FIGS. 13-16 illustrate another alternative embodiment of a segmented instrument having braking capabilities. The brake assembly 1400 is shown in use on an elongate body having a plurality of links 46. There is a hinge provided within the brake this embodiment of the brake assembly 1400 that connects a pair of adjacent links 46 as shown in FIGS. 13, 14 and 15B. The brake assembly 1400 is coupled to each link 46 in the pair of adjacent links and positioned to span the distance between the pair of adjacent links. Similar to the brake assembly 900, the brake assembly 1400 also includes components that have complementary shapes, provide for relative movement when the brake is not engage and multiply the number of friction surfaces when the brake 1400 is engaged. The individual components of the brake assembly 1400 are best seen in the views of FIGS. 15A and 16. The brake assembly 1400 includes a carrier plate 1410, a central sliding block 1405 and arms 1425 having arm sliders 1430. A lock plate 1440 (shown in FIGS. 14 and 14) is used to secure components to the carrier plate 1410. Returning to FIGS. 15A and 16, the arms 1425 include apertures 1435 for the common pivot pin 1420, best seen in FIG. 15A. Continuing to refer to FIG. 15A, pulling the cable 92 will decrease the spacing between central block 1405, arm sliders 1430 and base sliders 1415 and bring the complementary surfaces of these components into locking contact. Similar to the brake assembly 900, the added friction surfaces will act to enhance the locking capabilities provided by the brake assembly 1400. Both sides of the arm slider are engaged as it is compressed between the central sliding block 1405 and the base slider 1415.

FIGS. 14 and 15 provide additional views of a plurality of links 46 joined together by a number of brake assemblies 1400. FIG. 14 illustrates the cables 92A, 92B that may be used independently or in concert to actuate the brake assemblies 1400. FIG. 13 illustrates a central lumen 1470 in relation to the links 46. The central lumen 1470 could be another instrument, as would be the case when the plurality of links 46 shown is configured to act as a guide tube. Alternatively, the central lumen 1470 could be the interior components of a instrument (working channels, provisions for light, air, water and video capabilities commonly provided in endoscopy for example) when the plurality of links are configured as part of a controllable segmented instrument. In addition, control cables and other components described above and else where in this application would also be provided in order to provide steering control of the instrument formed by the links 46.

Figure 17:
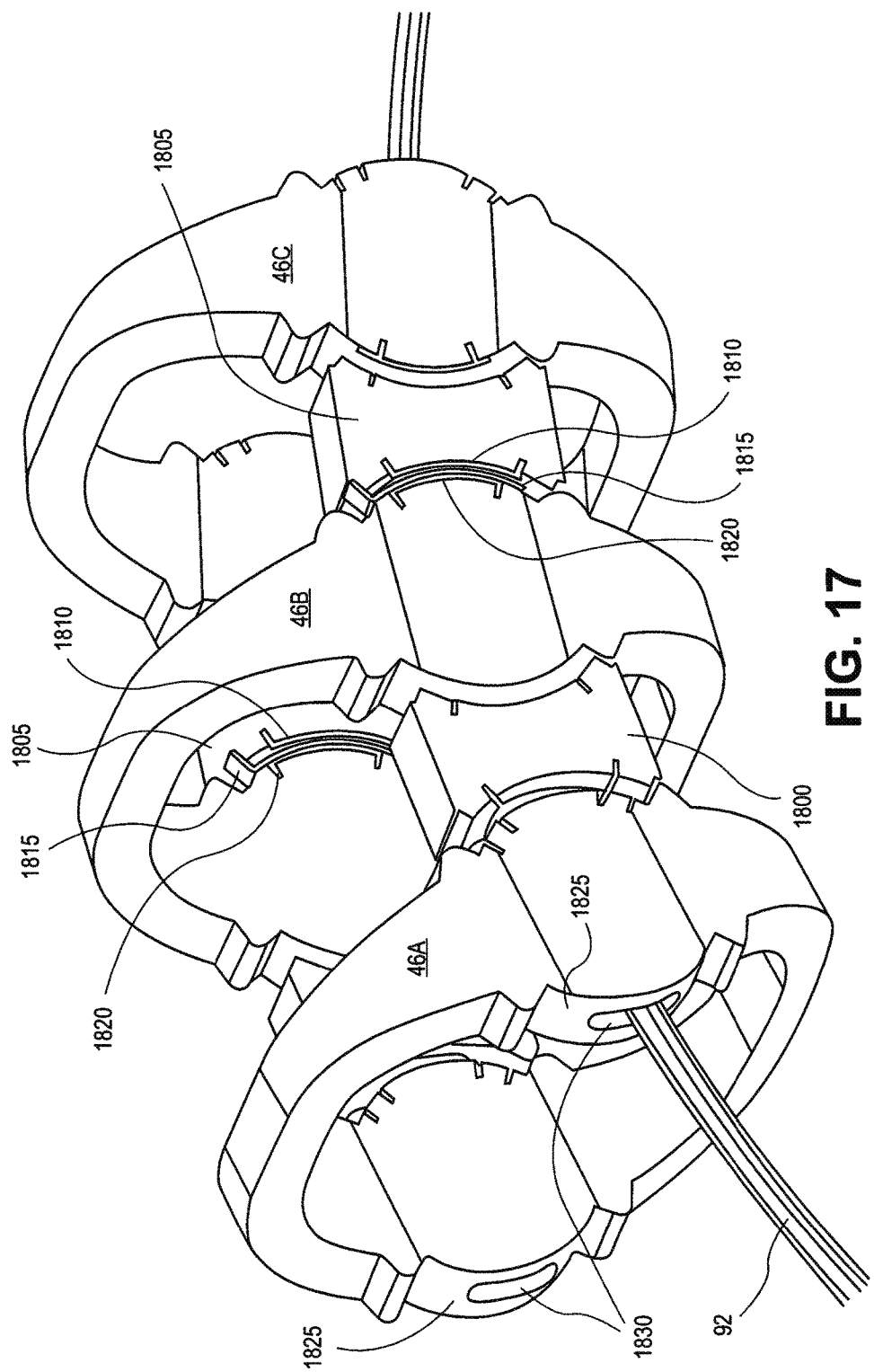
FIG. 17 illustrates an isometric view of another embodiment of a controllable instrument having braking capabilities.

FIG. 17 illustrates still another alternative embodiment of a brake assembly according to the present invention. FIG. 17 is an isometric view of a segmented instrument having braking capabilities provided by the brake assembly 1800. As shown, there is an elongate body having a plurality of links 46A, 46B and 46C. There is a hinge connecting a pair of adjacent links in the plurality of links provided by the brake assembly 1800. In addition, the brake assembly 1800 is coupled to each link in the pair of adjacent links and positioned to span the distance between the pair of adjacent links. In the illustrative embodiment, a brake assembly 1800 spans the distance between the link 46A and 46B and another brake assembly spans the distance between the links 46B and 46C. Similar to the previously described brake assemblies, the brake assembly 1800 provides articulation and locking capabilities between adjacent links. Moreover, the configuration and interoperability of the components of the brake assembly 1800 like the previous embodiments also provides an increased number of friction locking surfaces to enhance and magnify the applied locking force.

In the embodiment shown in FIG. 17, the brake assembly 1800 includes a central sliding block 1805. A base slider plate 1810 is attached to the central sliding block 1805. A center plate 1815 is also attached to the central sliding block 1805 and is positioned between the base slider plate 1810 and the hinge plate 1820 attached to the link 46B. The complementary surfaces of the central sliding block 1805, base slider 1810, center plate 1815 and the hinge plate 1820 allow for relative and sliding movement between these components, and the adjacent links 46 when the brake assembly 1800 is not engaged. When the brake assembly 1800 is engaged by pulling on the cable 92, the center plate is engaged between the base slider 1810 and the hinge plate 1820. In addition, the hinge plate 1820 is engaged to the complimentary surface 1825 of the link. The base slider is engaged against the complementary surface of the central sliding block 1805.

It is to be appreciated that the various braking assemblies described herein may be adapted and configured to operate in a number of different contexts. For example, the links and the brake assemblies may be configured to operate as an endoscope or other segmented controllable instrument. Additionally, the links and braking assemblies may be configured to function as a guide tube so that another instrument may pass through the central lumen of the links 46. In still other alternatives, the links and brake assemblies are configured into hybrid instruments having both highly controllable sections and the flexible and lockable sections. In one exemplary embodiment, there is one section of the instrument that is segmented and configured to be highly articulating with many degrees of freedom and optimum flexibility and controllability. Examples of such instruments are those instruments described above with regard to FIGS. 1-5. The proximal portion of that controllable instrument may be configured to be flexible and include locking assemblies. In this way, the hybrid instrument has articulation and control need in the surgical site while providing a proximal end that may be used as a base or support for the distal end.

Figure 18:
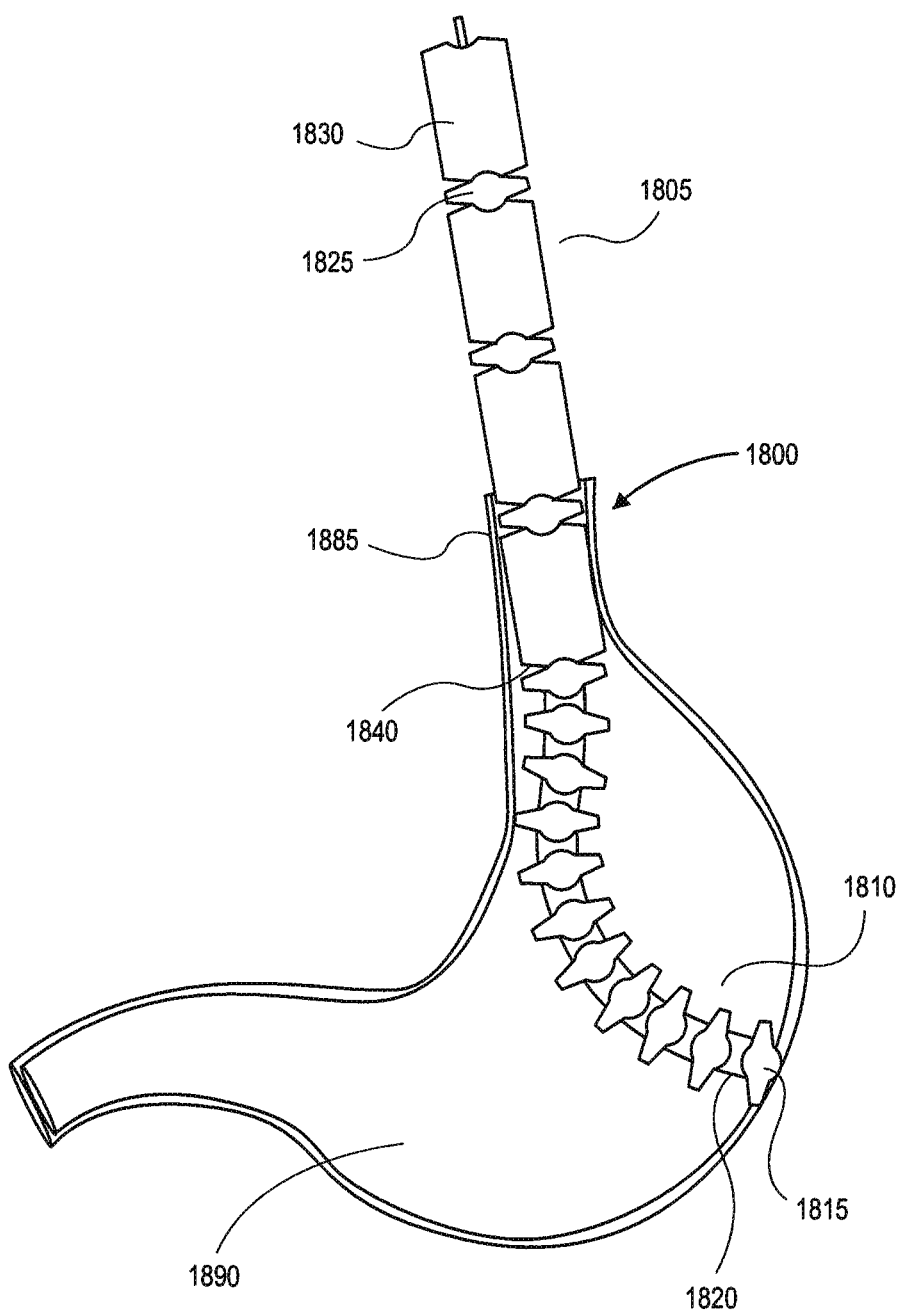
FIG. 18 illustrates an embodiment of an controllable instrument positioned within the esophagus and the stomach.

FIG. 18 is one exemplary embodiment of an instrument 1800 having a distal end 1810 and a proximal end 1805. The distal end includes hinges 1815 and flexible segments 1820. The proximal end 1805 includes flexible segments 1830 and articulating brake assemblies 1825. The proximal end segments 1830 are larger than the segments 1820 because the distal end in this embodiment is configured for greater articulation and control capabilities. In addition, the change in the size of the segments and control of the instrument or function of the instrument changes at the flexible-base transition 1840. As shown in the illustrative embodiment of FIG. 18, the instrument 1800 is positioned in the alimentary canal with the distal end positioned just prior to forming an opening in the stomach 1890 in furtherance of a transgastric or transluminal or other NOTES procedure. Once the opening is formed and the distal end is advanced, the distal end of highly articulating end could be advanced through the opening up to or beyond the transition point 1840. While the proximal end may be advanced through the transluminal opening, there are configurations where the relative lengths of the proximal and distal ends are selected so that when the distal section is in the surgical site the proximal end in positioned and locked within the esophagus 1885 and stomach 1890 to provide a base for the operation of the articulating distal end 1810. In still other embodiments, the hinges 1815 may also be configured as brake assemblies as described herein so that the distal end may articulate, including computer controlled articulation as described herein, and also have the enhanced locking capabilities of the brake assemblies of the present invention.

Figure 19:
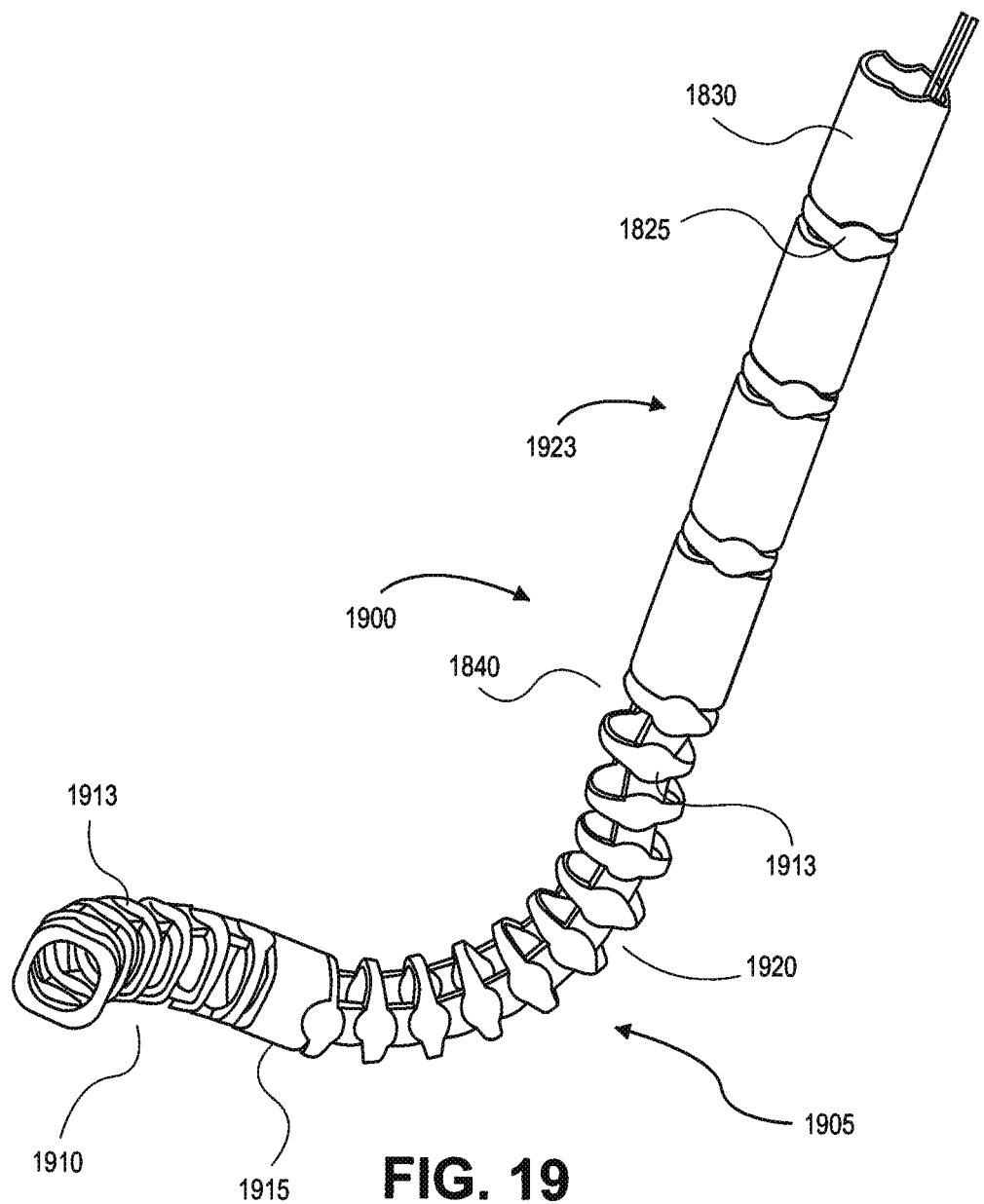
FIG. 19 illustrates an embodiment of a controllable instrument having a distal section with articulatable and lockable segments in different orientations.

FIG. 19 is another exemplary embodiment of an instrument 1900 having a distal end 1905 and a proximal end 1823. The distal end 1905 includes hinges 1913 and flexible segments. The distal end 1905 is divided into a distal section 1910 where the hinges 1913 are aligned to provide articulation in a first orientation and a proximal section 1920 where the hinges 1913 are aligned to provide articulation in a second orientation. The transition section 1915 is adapted and configured to provide the transition between the different orientations of the articulation in the distal section 1910 and the proximal section 1920. Similar to the embodiment in FIG. 18, the instrument 1900 also includes a proximal end 1923 that includes flexible segments 1830 and articulating brake assemblies 1825. As before, the proximal end segments 1830 are larger than the segments 1820 because the distal end in this embodiment is configured for greater articulation and control capabilities. In addition, the change in the size of the segments and control of the instrument or function of the instrument changes at the flexible-base transition 1840. As with the embodiment of FIG. 18 and the other embodiments, the embodiment of instrument 1900 may be placed in the alimentary canal with the distal end positioned just prior to forming an opening in the stomach in furtherance of a transgastric or transluminal or other NOTES procedure. Once the opening is formed and the distal end is advanced, the distal end 1905 may be advanced through the opening up to or beyond the transition point 1840. While the proximal end 1923 may be advanced through the transluminal opening, there are configurations where the relative lengths of the proximal and distal ends are selected so that when the distal section is in the surgical site the proximal end in positioned and locked within the esophagus 1885 and stomach 1890 to provide a base for the operation of the articulating distal end 1905. In still other embodiments, the hinges 1913, 1825 may also be configured as brake assemblies as described herein so that the distal end may articulate, including computer controlled articulation as described herein, and also have the enhanced locking capabilities of the brake assemblies of the present invention. It is to be appreciated that the orientations between the distal sections 1910, 1920 may be changed or specifically adapted for a particular procedure or NOTES access site.

While reference has been made to the use of the instruments described herein in either their articulating or lockable forms as accessing a surgical site via the stomach, the uses of the invention are not so limited. Embodiments of the present invention may be modified and adapted as needed to facilitate entry and access to surgical site via natural orifice (such as, for example, through the mouth, the anus/colon or the vagina or other openings formed once the instrument has accessed the alimentary canal), surgically created openings including laparoscopic or single port access openings or other percutaneous openings. In addition, other embodiments of the instruments having braking capabilities as described herein may be configured as rigidizable external working channels as well as rigidizable external working channels that can be separated from another scope or instrument.

In another aspect of the invention, the segmented instrument with braking capabilities may also be used to aid a physician in the performance of a surgical procedure. This aspect includes a method of controlling a segmented instrument. First, there is a step of introducing a segmented instrument into a patient, the segmented instrument having a plurality of links wherein adjacent links are joined by a hinge. Next, there is a step of manipulating the links about the hinges to maneuver the segmented instrument to provide access to a surgical site within the patient. In one aspect, the manipulating step produces a sliding motion between a plurality of complementary shaped components within a portion of a brake assembly between adjacent links. Next, there is also a step of actuating the brake assembly to substantially prevent movement about the hinge of the links attached to the braking mechanism.

As will be appreciated from the discussion above, the actuating step in the method of controlling a segmented instrument may take any of several forms. For example, the actuating step may include applying vacuum to the interior of the segmented instrument. Alternatively, the actuating step comprises pulling a cable. It is to be appreciated that the actuating step substantially locks the shape of a portion of the controllable instrument.

Depending upon specific circumstances where the segmented instrument is being used, the method of controlling a segmented instrument may also include advancing a surgical implement through a working channel in the segmented instrument to the surgical site. Additionally or alternatively, the advancing step is performed after the actuating step. In still other alternative methods, there is also a step of accessing the surgical site with a controllable surgical instrument advanced through the segmented instrument. In addition, the advancing step is performed before, after or during the actuating step.

It is to be appreciated that the inventive brake assemblies described herein may be applied to the guide tubes and controllable segmented instruments and used in the various methods described in the co-pending and commonly assigned application "METHODS AND APPARATUS FOR PERFORMING TRANSLUMINAL AND OTHER PROCEDURES" filed on Sep. 14, 2006 as application Ser. No. 11/522,305, now published patent application number US 2007-0135803 (published on Jun. 14, 2007). In addition, the brake assemblies and other details described herein may also be configured and controlled as those instruments in and used to perform the surgical procedures described in the commonly assigned and co-pending "APPARATUS AND METHODS FOR AUTOMATICALLY CONTROLLING AN ENDOSCOPE" filed on Jan. 29, 2009 as PCT/US2009/032481.

What is claimed is:

1. A segmented instrument having braking capabilities, comprising:
   an elongate body defining a central lumen extending from a proximal end to a distal end of the elongate body, the central lumen being sized to receive and advance a surgical instrument through the elongate body to a location beyond the distal end of the elongate body, the elongate body comprising:
   a plurality of links disposed in series along an axial direction of the elongate body, the plurality of links comprising a pair of adjacent links having opposing arcuate mating surfaces;
   an arm pivotably coupling the pair of adjacent links in the plurality of links to one another via a pin joint at each link of the pair of adjacent links; and
   a brake assembly coupled to each link in the pair of adjacent links and positioned-between the pair of adjacent links, wherein the brake assembly comprises a first component and a second component disposed consecutively in the axial direction, each of the first component and the second component comprising an aperture through which the arm extends, the first component having a first surface configured to mate with the arcuate mating surface of one of the pair of adjacent links and the second component having a second surface configured to mate with the arcuate mating surface of the other of the pair of adjacent links, the first and second components being configured to move relative to each other in a first state of the brake assembly and being configured to engage each other to prevent each link of the pair of adjacent links from moving relative to each other in a second state of the brake assembly, and
   wherein the brake assembly is placed in the second state by a force applied along an axial direction of the pair of adjacent links.

2. The segmented instrument according to claim 1, wherein the first component and second component comprise a component positioned adjacent one link in the pair of links that moves along with movement of another of the links in the pair of links.

3. The segmented instrument according to claim 1, wherein the brake assembly is placed in the second state by pulling on a cable to apply the force along the axial direction of the pair of adjacent links.

4. The segmented instrument according to claim 1, wherein only a portion of the plurality of links includes the brake assembly.

5. The segmented instrument according to claim 4, wherein the portion of the plurality of links is a distal portion of the plurality of links.

6. The segmented instrument according to claim 4, wherein the portion of the plurality of links is a proximal portion of the plurality of links.

7. The segmented instrument according to claim 4, wherein the portion of the plurality of links is a middle portion of the plurality of links.

8. The segmented instrument according to claim 1, wherein actuation of the brake assembly to the second state removes one degree of freedom from a portion of the instrument.

9. The segmented instrument according to claim 1, further comprising a plurality of brake assemblies coupled to the instrument, wherein actuation of the plurality of brake assemblies to the second state substantially locks a shape of the instrument by locking substantially all of the plurality of links in the instrument.

10. The segmented instrument according to claim 1, further comprising a plurality of brake assemblies coupled to the instrument, wherein actuation of the plurality of brake assemblies to the second state substantially removes one degree of freedom of movement of the segmented instrument.

11. A method of controlling movement of a segmented instrument, comprising:
introducing a segmented instrument into a patient, the segmented instrument having a plurality of links, each link of the plurality of links having opposing ends with arcuate mating surfaces, wherein adjacent links of the plurality of links are joined by a hinge;
manipulating the links about the hinges to maneuver the segmented instrument to provide access to a surgical site within the patient, wherein the manipulating produces a sliding motion of a first component and a second component of a brake assembly relative to one another in a first state of the brake assembly, wherein the first component and the second component are positioned consecutively along an axial direction of the segmented instrument in a space between the adjacent links and configured to mate with the arcuate mating surfaces of the links; and
actuating the brake assembly to engage the first component and the second component with each other in a second state of the brake assembly and to substantially prevent movement about the hinge, wherein the actuating comprises applying a force along an axial direction of the adjacent links.

12. The method of controlling movement of a segmented instrument according to claim 11, wherein the actuating comprises pulling a cable.

13. The method of controlling movement of a segmented instrument according to claim 11, wherein the actuating substantially locks a shape of a portion of the controllable instrument.

14. The method of controlling movement of a segmented instrument according to claim 11, further comprising:
advancing a surgical implement through a working channel in the segmented instrument to the surgical site.

15. The method of controlling movement of a segmented instrument according to claim 14, wherein the advancing is performed after the actuating and with the brake assembly in the first state.

16. The method of controlling movement of a segmented instrument according to claim 14, further comprising:
accessing the surgical site with a controllable surgical instrument advanced through the segmented instrument.

17. The method of controlling movement of a segmented instrument according to claim 16, wherein the advancing is performed after the actuating and with the brake assembly in the first state.

18. A segmented instrument, comprising:
a plurality of links disposed in series along an axial direction of the instrument, the plurality of links defining a central lumen extending from a proximal end to a distal end of the segmented instrument, the central lumen being sized to receive and advance a surgical instrument through the segmented instrument to a location beyond the distal end of the segmented instrument; and
at least one lockable and articulatable joint positioned to connect a pair of consecutively disposed links in the plurality of links,
wherein the at least one lockable and articulatable joint comprises a plurality of components positioned in a space between the pair of consecutively disposed links and an arm pivotably coupled via pin joints at opposite ends to the pair of consecutively disposed links, wherein each component of the plurality of components comprises an aperture through which the arm extends,
wherein three frictional interfaces are consecutively disposed along the axial direction of the segmented instrument between the pair of consecutively disposed links, the frictional interfaces being respectively defined by complementary surfaces of adjacent components of the plurality of components and by complementary surfaces of at least one component of the plurality of components and at least one link of the pair of consecutively disposed links,
wherein the complementary surfaces of each frictional interface move relative to each other in a first, unlocked state of the joint and engage each other in response to an axially directed force to prevent the pair of consecutively disposed links from moving relative to each other in a second, locked state of the joint.

19. The segmented instrument according to claim 1, wherein the first component and second component are moveably coupled to the links of the pair of adjacent links.

20. The segmented instrument according to claim 1, wherein the first surface and second surface are respective complementary concave and convex surfaces.

21. The segmented instrument according to claim 18, wherein the plurality of components span the space between the pair of consecutively disposed links.

22. The segmented instrument according to claim 18, wherein at least a portion of each of the frictional interfaces is oriented substantially perpendicular to a longitudinal axis of the joint.

23. The method according to claim 11, wherein the plurality of links is disposed in series along an axial direction of the segmented instrument, and wherein the arcuate mating surfaces are axially spaced from each link of the adjacent links.

* * * * *